(12) United States Patent
Choo et al.

(10) Patent No.: US 11,629,367 B2
(45) Date of Patent: Apr. 18, 2023

(54) SYSTEMS AND METHODS FOR PRODUCTION OF RECOMBINANT IL-11 IN YEAST

(71) Applicant: Nansha Biologies (Hong Kong) Limited, Central (HK)

(72) Inventors: Qui-Lim Choo, El Cerrito, CA (US); Manson Fok, The Peak (HK); Johnson Yiu-Nam Lau, Houston (CA)

(73) Assignee: Nansha Biologies (HK) Limited, Hong Kong (CN)

( * ) Notice: Subject to any disclaimer, the term of this patent is extended or adjusted under 35 U.S.C. 154(b) by 522 days.

(21) Appl. No.: 16/478,108

(22) PCT Filed: Jan. 15, 2018

(86) PCT No.: PCT/US2018/013708
§ 371 (c)(1),
(2) Date: Jul. 15, 2019

(87) PCT Pub. No.: WO2018/132787
PCT Pub. Date: Jul. 19, 2018

(65) Prior Publication Data
US 2021/0317500 A1 Oct. 14, 2021

Related U.S. Application Data

(60) Provisional application No. 62/446,762, filed on Jan. 16, 2017.

(51) Int. Cl.
*C12P 21/02* (2006.01)
*C07K 14/54* (2006.01)

(52) U.S. Cl.
CPC .......... *C12P 21/02* (2013.01); *C07K 14/5431* (2013.01)

(58) Field of Classification Search
None
See application file for complete search history.

(56) References Cited

U.S. PATENT DOCUMENTS

| | | |
|---|---|---|
| 5,646,016 A | 7/1997 | McCoy et al. |
| 6,066,317 A | 5/2000 | Yang |
| 8,133,480 B2 | 3/2012 | Cox, III |
| 2007/0111240 A1 | 5/2007 | Cox |
| 2008/0069796 A1 * | 3/2008 | Kim .................. A61K 38/2073 424/85.2 |
| 2010/0098658 A1 | 4/2010 | Jung et al. |

FOREIGN PATENT DOCUMENTS

| | | | |
|---|---|---|---|
| CN | 1203920 | 1/1999 | |
| CN | 1288062 A | 3/2001 | |
| CN | 1203920 C | 6/2005 | |
| CN | 201110293041 | 1/2012 | |
| CN | 102329388 B | 7/2013 | |
| EP | 0504751 A1 * | 9/1992 | ......... C07K 14/5412 |
| JP | 2005281302 | 10/2005 | |
| KR | 100426286 B1 | 6/2004 | |
| WO | 97232208 | 7/1997 | |
| WO | 2011113601 | 9/2011 | |
| WO | 2011151716 | 12/2011 | |
| WO | 2012063182 | 5/2012 | |
| WO | 2013020079 | 2/2013 | |

OTHER PUBLICATIONS

Lodish et al (Lodish H, Berk A, Zipursky SL, et al. New York: W. H. Freeman; 2000) (Year: 2000).*
Graslund et al (Nat Methods. Feb. 2008 ; 5(2): 135-146) (Year: 2008).*
Li et al (FEMS Yeast Res 11 (2011) 160-167) (Year: 2011).*
Bahrami A., et al., "Prevention of Human Granulocyte Colony-stimulating Factor Protein Aggregation in Recombinant Pichia Pastoris Fed-batch Fermentation Using Additives", Biotechnology and Applied Biochemistry, 2009, vol. 52, pp. 141-148.
Consequences and Transgenic Milk Prospects Turn Sour, Nature Biotechnology, Apr. 2006, vol. 24 (4), pp. 368.
Du X.X., et al., "Interleukin-11: A Multifunctional Growth Factor Derived From the Hematopoietic Microenvironment", Blood, Apr. 15, 1994, vol. 83 (8), pp. 2023-2030, [Retrieved on Jan. 15, 2018] Retrieved from the internet [URL: http://www.bloodjournal.org].
Farr S.B., et al., "Oxidative Stress Responses in *Escherichia coli* and *Salmonella typhimurium*", Microbiological Reviews, Dec. 1991, vol. 55 (4), pp. 561-585, [Retrieved on Jan. 15, 2018] Retrieved from the Internet [URL: http://mmbr.asm.org/].
Gasteiger E., et al., "Protein Identification and Analysis Tools on the ExPASy Server," The Proteomics Protocols Handbook, USA, In: Walker JM, editor, Humana Press Inc., 2005, pp. 571-607.

(Continued)

*Primary Examiner* — Brian Gangle
*Assistant Examiner* — Andrea K McCollum
(74) *Attorney, Agent, or Firm* — Fish IP Law, LLP

(57) ABSTRACT

Recombinant interleukin-11 (rhIL-11) is expressed in yeast, then isolated from aerobic fermentation media by precipitation, solubilization of the precipitate in the presence of a denaturant, and renaturation of the solubilized protein. Renatured rhIL-11 is further purified by cation exchange and hydrophobic interaction chromatography to provide a highly purified rhIL-11 with high biological activity and low rhIL-11 dimer and oxidized rhIL-11 content.

11 Claims, 19 Drawing Sheets
Specification includes a Sequence Listing.

(56) References Cited

OTHER PUBLICATIONS

Hart R.A., et al., "Large Scale, in Situ Isolation of Periplasmic IGF-I From *E. coli*," Biotechnology, Nov. 1994, Nature Publishing Company, vol. 12 (11), pp. 1113-1117.

Hong E., et al., "A Pathyway for Targeting Soluble Misfolded Proteins to the Yeast Vacuole", The Journal of Cell Biology, Nov. 1996, vol. 135 (3), pp. 623-633, [Retrieved on Jan. 15, 2018] Retrieved from the Internet [URL: icb.rupress.org].

International Search Report and Written Opinion for Application No. PCT/US2018/013708, dated May 1, 2018, 12 pages.

Karow J., et al., "Mediation of Interleukin-11-dependent Biological Responses By A Soluble Form of the Interleukin-11 Receptor", Biochemical Journal, 1996, vol. 318, pp. 489-495.

Li H., et al., "Large-scale Production, Purification and Bioactivity Assay of Recombinant Human Intedeukin-6 in Themethylotrophic Yeast Pichia Pastoris" Yeast Research, Federation of European Microbiological Societies (FEMS), 2011, vol. 11, pp. 160-167, [Retrieved on Jul. 12, 2019] Retrieved from the Internet [URL: https://academic.oup.com/femsyr/article-abstract/11/2/160/588634].

Ozols J., "Amino Acid Analysis", Methods in Enzymology, 1990, vol. 182 (44), pp. 587-601.

Shacter E., "Quantification and Significance of Protein Oxidation in Biological Samples", Drug Metabolism Reviews, 2000, vol. 32 (3&4), pp. 307-326.

Tsumoto K., et al., "Practical Considerations in Refolding Proteins from Inclusion Bodies", Protein Expression and Purification, 2003, vol. 28, pp. 1-8.

Yokota H., et al., "Reversed Phase HPLC of Met58 Oxidized rhIL-11: Oxidation Enhanced by Plastic Tubes", , Journal of Pharmaceutical and Biomedical Analysis, 2000, vol. 24, pp. 317-324.

Li, Hongbo, et al. "Large-scale production, purification, and bioactivity assay of recombinant human interleukin-6 in the methylotrophic yeast Pichia pastoris," FEMS Yeast Research. Dec. 22, 2010. 8 pages.

Extended European Search Report dated Nov. 24, 2020, from related EP application No. 18739114.9. 11 pages.

Yamaguchi, Hiroshi, et al. "Refolding Techniques for Recovering Biologically Active Recombinant Proteins from Inclusion Bodies," Biomolecules. Feb. 20, 2014. 17 pages.

Widjaja, et al. "Different roles of interleukin 6 and interleukin 11 in the liver: implications for therapy," Human Vaccines and Immunotherapies 2020, vol. 16, No. 10, 2357-2362. 6 pages.

Gao, et al. "Process control and physiological analysis of heterologous protein production by recombinant Pichia pastoris," School of Biotechnology, Jiangnan University. vol. 35, No. 24, 2014. 7 pages.

Yu, et al. "Efficient expression and isolation of recombinant human interleukin-11 (rhIL-11) in Pichia pastoris," Protein Expression and Purification 146 (2018) 69-77. 9 pages.

Huang, et al. Purification and characterization of recombinant human interleukin 11 which extressed by Pichia pastoris, Chinese Journal of Biotechnology, 2001, vol. 17, No. 3: 250-253.

Zhu, et al. "Expression and purification of recombinant human interleukin-11 in Pichia pastoris,", Acta Academiae Medicinae Sinicae, 2001, vol. 23, No. 2: 127-31.

Wang, et al. "Exuression of the recombinant human interleukin-11 in Pichia pastoris,", Acta Biochimica et Biophysica Sinica, 2001, vol. 33, No. 6, pp. 659-664.

\* cited by examiner

M: Protien marker
1: medium
2: 6.2% PEG-8000 supernatent
3: 7.3% PEG-8000 supernatent
4: 8.2% PEG-8000 supernatent
5: 6.2% PEG-8000 precipitate
6: 7.3% PEG-8000 precipitate
7: 8.2% PEG-8000 precipitate

SEQUENCE LISTING

```
<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
<223> OTHER INFORMATION: peptide fragment of recombinant IL-11

<400> SEQUENCE: 1

Gly Pro Pro Pro Gly Pro Pro Arg
1               5

<210> SEQ ID NO 2
<211> LENGTH: 6
<212> TYPE: PRT
<213> ORGANISM: Artificial Sequence
<220> FEATURE:
<223> OTHER INFORMATION: peptide fragment of recombinant IL-11

<400> SEQUENCE: 2

Val Ser Pro Asp Pro Arg
1               5
```

```
<210> SEQ ID NO 3
<211> LENGTH: 11
<212> TYPE: PRT
<213> ORGANISM: Artificial Sequence
<220> FEATURE:
<223> OTHER INFORMATION: peptide fragment of recombinant IL-11

<400> SEQUENCE: 3

Ala Glu Leu Asp Ser Thr Val Leu Leu Thr Arg
1               5                   10

<210> SEQ ID NO 4
<211> LENGTH: 7
<212> TYPE: PRT
<213> ORGANISM: Artificial Sequence
<220> FEATURE:
<223> OTHER INFORMATION: peptide fragment of recombinant IL-11

<400> SEQUENCE: 4

Ser Leu Leu Ala Asp Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: peptide fragment of recombinant IL-11

<400> SEQUENCE: 5

Gln Leu Ala Ala Gln Leu Arg
1               5

<210> SEQ ID NO 6
<211> LENGTH: 20
<212> TYPE: PRT
<213> ORGANISM: Artificial Sequence
<220> FEATURE:
<223> OTHER INFORMATION: peptide fragment of recombinant IL-11

<400> SEQUENCE: 6

Phe Pro Ala Asp Gly Asp His Asn Leu Asp Ser Leu Pro Thr Leu Ala
1               5                   10                  15

Met Ser Ala Gly
            20

<210> SEQ ID NO 7
<211> LENGTH: 8
<212> TYPE: PRT
<213> ORGANISM: Artificial Sequence
<220> FEATURE:
<223> OTHER INFORMATION: peptide fragment of recombinant IL-11

<400> SEQUENCE: 7

Ala Asp Leu Leu Ser Tyr Leu Arg
1               5

<210> SEQ ID NO 8
<211> LENGTH: 6
<212> TYPE: PRT
<213> ORGANISM: Artificial Sequence
<220> FEATURE:
<223> OTHER INFORMATION: peptide fragment of recombinant IL-11

<400> SEQUENCE: 8

His Val Gln Trp Leu Arg
1               5
```

<210> SEQ ID NO 9
<211> LENGTH: 7
<212> TYPE: PRT
<213> ORGANISM: Artificial Sequence
<220> FEATURE:
<223> OTHER INFORMATION: peptide fragment of recombinant IL-11

<400> SEQUENCE: 9

Ala Gly Gly Ser Ser Leu Lys
1               5

<210> SEQ ID NO 10
<211> LENGTH: 12
<212> TYPE: PRT
<213> ORGANISM: Artificial Sequence
<220> FEATURE:
<223> OTHER INFORMATION: peptide fragment of recombinant IL-11

<400> SEQUENCE: 10

Thr Leu Glu Pro Glu Leu Gly Thr Leu Gln Ala Arg
1               5                   10

<210> SEQ ID NO 11
<211> LENGTH: 7
<212> TYPE: PRT
<213> ORGANISM: Artificial Sequence
<220> FEATURE:
<223> OTHER INFORMATION: peptide fragment of recombinant IL-11

<400> SEQUENCE: 11

Leu Gln Leu Leu Met Ser Arg
1               5

<210> SEQ ID NO 12
<211> LENGTH: 26
<212> TYPE: PRT
<213> ORGANISM: Artificial Sequence
<220> FEATURE:
<223> OTHER INFORMATION: peptide fragment of recombinant IL-11

<400> SEQUENCE: 12

Leu Ala Leu Pro Gln Pro Pro Pro Asp Pro Pro Ala Pro Pro Leu Ala
1               5                   10                  15
Pro Pro Ser Ser Ala Trp Gly Gly Ile Arg
            20                  25

<210> SEQ ID NO 13
<211> LENGTH: 18
<212> TYPE: PRT
<213> ORGANISM: Artificial Sequence
<220> FEATURE:
<223> OTHER INFORMATION: peptide fragment of recombinant IL-11

<400> SEQUENCE: 13

Ala Ala His Ala Ile Leu Gly Gly Leu His Leu Thr Leu Asp Trp Ala
1               5                   10                  15
Val Arg

<210> SEQ ID NO 14
<211> LENGTH: 6
<212> TYPE: PRT
<213> ORGANISM: Artificial Sequence
<220> FEATURE:
<223> OTHER INFORMATION: peptide fragment of recombinant IL-11

```
<400> SEQUENCE: 14

Gly Leu Leu Leu Leu Lys
1               5

<210> SEQ ID NO 15
<211> LENGTH: 15
<212> TYPE: PRT
<213> ORGANISM: Artificial Sequence
<220> FEATURE:
<223> OTHER INFORMATION: N-terminal peptide fragment of recombinant
      IL-11

<400> SEQUENCE: 15

Gly Pro Pro Pro Gly Pro Pro Arg Val Ser Pro Asp Pro Arg Ala
1               5                   10                  15
```

SYSTEMS AND METHODS FOR PRODUCTION OF RECOMBINANT IL-11 IN YEAST

This application claims the benefit of U.S. Provisional Application No. 62/446,762, filed on Jan. 16, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is production and subsequent purification of recombinant IL-11, particularly in yeast.

BACKGROUND

The background description includes information that may be useful in understanding the present invention. It is not an admission that any of the information provided herein is prior art or relevant to the presently claimed invention, or that any publication specifically or implicitly referenced is prior art.

The interleukin IL-11 has considerable therapeutic potential, however production of IL-11 at adequate scale and purity has proven challenging. Due to the lack of glycosylation expression of recombinant IL-11 in bacteria has been attempted. The resulting protein, however, tends to be expressed as insoluble inclusion bodies, resulting in poor yields. This is probably due to improper folding. Attempts have been made to express IL-11 in yeast, however to date such processes have provided low yields and have required the use of toxic organic solvents.

One approach to address this is to express recombinant IL-11 as a fusion protein having more desirable expression characteristics. Commercially available IL-11 is typically isolated from a fusion protein expressed in *E. coli*. Unfortunately the use of enterokinase to generate an IL-11 fragment from the fusion protein results in product heterogeneity. Similarly, United States Patent Application Publication No. 2009/0010872 (to Mackiewicz) describes a recombinant IL-11 fusion protein that incorporates both IL-11 and soluble IL-11 receptor sequences and expression of such a fusion protein in insect or mammalian cells in culture. Recovery of IL-11 from such a fusion protein, however, requires additional processing steps that cleave the fusion protein and can result in variations in the length and/or sequence of the product IL-11 fragment. In addition such cells have complex culture requirements that can complicate downstream purification of the desired product.

For example United States Patent Application Publication No. 2007/0275889 describes the use of a plasmid encoding for both an IL-11 sequence and a chaperonin, and expression of such a plasmid in insect or mammalian cells in culture. The chaperonin serves to provide proper folding and prevent aggregation of the expressed IL-11. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. As noted above, however, culture conditions for such cells can complicate subsequent purification steps. In addition, expression in mammalian and insect cells in culture is generally far lower than that of bacteria or yeast.

Thus, there is still a need for a simple, effective, and scalable method for providing substantially pure and active IL-11.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

The inventive subject matter provides apparatus, systems and methods that provide a highly purified recombinant IL-11 with reduced dimer and oxidation content relative to prior art methods.

One embodiment of the inventive concept is a method for producing IL-11 that includes introducing an expression vector encoding for a recombinant IL-11 into a yeast, where the encoded recombinant IL-11 is not in the form of a fusion protein. The yeast is cultured in a culture media under conditions that induce expression of the IL-11, and subsequently a supernatant is separated from solids of the culture media. This supernatant is then treated with polyethylene glycol in quantities sufficient to form a suspension that includes a precipitate. For example, polyethylene glycol can be provided at a final concentration of about 4% (w/v) to about 12% (w/v) and/or about 6% (w/v) to about 9% (w/v). Such polyethylene glycol can have a molecular weight ranging from about 2,000 D to about 20,000 D, and/or from about 4,000 D to about 12,000 D.

This precipitate is solubilized in a solution that includes a denaturant, producing a crude IL-11 solution. Suitable denaturants include urea, guanidine hydrochloride, and/or a detergent (such as a dodecyl sulfate salt and/or an N-sarcosyl). For example, the concentration of guanidine hydrochloride can be at a concentration of about 4M to about 10M or about 5M to about 9M in such a solubilizing step. The denaturant concentration is then reduced (for example, guanidine hydrochloride concentration can be reduced to 0.7M or less) to produce a refolded IL-11 solution. In some embodiments the step of reducing the denaturant concentration includes incubating for about one hour at 18° C. to 25° C. following reduction of the denaturant concentration. The concentration of denaturant can be reduced by any suitable means, including dilution and/or buffer exchange. Refolding of the IL-11 can be performed at a protein concentration of about 0.1 mg/mL to about 10 mg/mL, and/or less than about 2 mg/mL, and can be performed without co-solutes. Refolding can be performed at a pH of about 4 to about 12, or at a pH of about 7 to about 11. The refolded IL-11 solution is then brought into contact with an ion exchange media, and a purified IL-11 is subsequently eluted from the ion exchange media (e.g. a cation exchange media).

In some embodiments the above described method includes additional processing steps. In some embodiments the purified IL-11 is brought into contact with a hydrophobic interaction media. Suitable hydrophobic interaction media include butyl, hexyl, octyl, and/or phenyl media. A polished IL-11, which has a reduced content of oxidized IL-11 relative to the purified IL-11, is subsequently eluted from the hydrophobic interaction media. The resulting purified IL-11 can have a purity of at least 95%, for example including about 5% or less oxidized IL-11 and/or 1% or less dimers of IL-11. The polished IL-11 typically has a biological activity of about $4\times10^6$ U/mg to about $1.2\times10^7$ U/mg (for example, about $6\times10^6$ U/mg) when tested using a 7TD1 cell line.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A depicts a growth curve throughout different time points. Culture medium at different post-induction time points was harvested and analyzed by non-reducing SDS-PAGE and immunoblotting. FIG. 1B shows typical results of non-reducing SDS-PAGE with Coomassie blue staining. FIG. 1C shows typical results from Western immunoblotting. M represents protein marker.

FIG. 6A shows results from the use of 8M urea. FIG. 6B shows results from the use of 6M guanidine hydrochloride. In both figures the red trace depicts in-line conductivity and the blue trace depicts UV absorbance at 280 nm. Arrows indicate the elution position of the renatured rhIL-11.

FIG. 11A shows a typical ion chromatogram. FIG. 11B shows a major peak with a deconvoluted mass of 19,046.7 Da, which agrees with the expected molecular weight 19,047. The minor peak observed at a deconvoluted mass of 19,062.5 Da is presumably oxidized IL-11, as the additional 16 Da can be accounted for by a single oxygen.

DETAILED DESCRIPTION

Figure 1A:
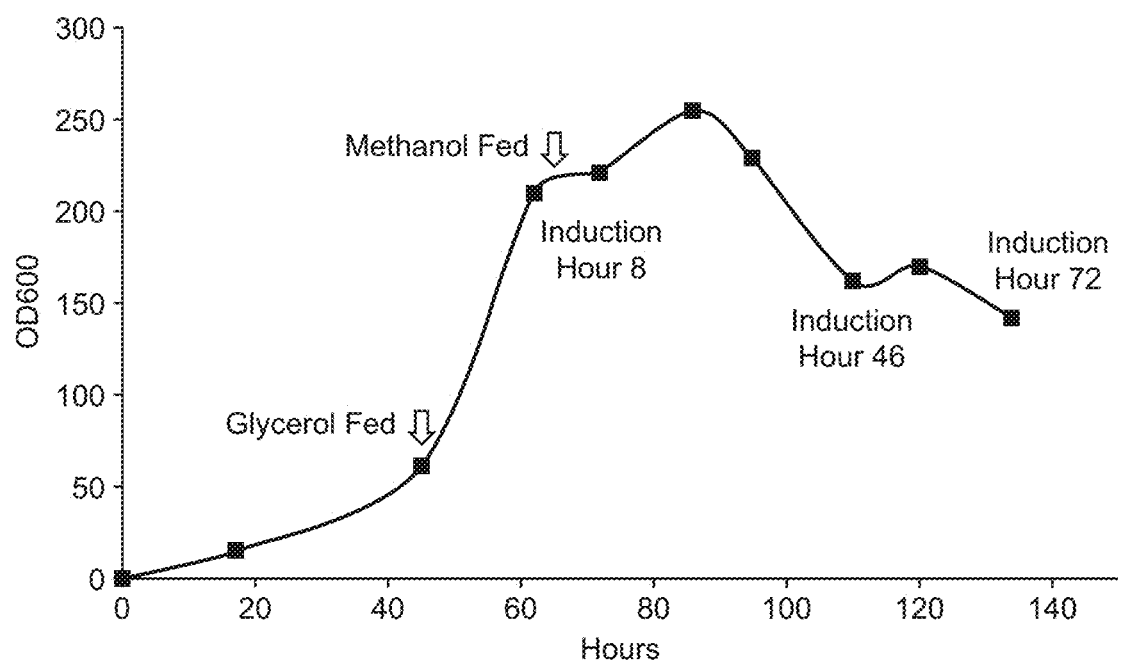
FIGS. 1A to 1C depict results of high density fermentation of rhIL-11 expression.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which a recombinant human IL-11 can be expressed in yeast and recovered from culture media as an active, substantially pure, monomeric protein. The recombinant protein is precipitated using a solvent excluding reagent (such as polyethylene glycol), solubilized in the presence of a chaotrope or denaturant (such as guanidinium), and renatured to provide proper protein folding. Chromatographic steps, such as ion exchange (e.g. cation exchange) and/or hydrophobic interaction chromatography (e.g. using a butyl-substituted chromatography medium) can be incorporated into methods of the inventive concept.

Various objects, features, aspects and advantages of the inventive subject matter will become more apparent from the following detailed description of preferred embodiments, along with the accompanying drawing figures in which like numerals represent like components.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In deriving methods and compositions of the inventive concept, PICHIAPINK™ Expression System from Invitrogen was used for establishing stable rhIL-11 high-level expressing clones that secrete rhIL-11. The vector expresses an α-mating factor pre-sequence from *Saccharomyces cerevisiae*, which is a short signaling peptide guiding recombinant protein to the extracellular medium. A special feature of the PICHIAPINK™ Expression System is the use of ADE2 gene promoter and gene product for selection of high copy number clones. Mutation of ADE2, the gene responsible for de novo biosynthesis of purine nucleotides, results in accumulation of purine precursors that provide transformed colonies with a red/pink color. The expression strains are ade2 auxotrophs which are unable to grow on medium lacking adenine. Transformation of an expression host with plasmids enables the strain to grow on medium lacking adenine, and the short ADE promoter sequence facilitates the screening of clones with high copy number integrated. Colonies with low copy number appear pink; whereas white colonies are high copy number clones.

Prior art methods of producing recombinant human IL-11 in yeast using *Pichia pastoris* suffer from low production yields at the yeast expression level as well as at the product purification level. Inventors found that results from high cell-density fermentation suggested both expression of inactive rhIL-11 and low recovery yield (1-5%) after cation-exchange purification. ELISA quantitation of expression level in medium was found to underestimate IL-11 content (by approximately 90% reduction) when compared to SDS-PAGE analysis against references of known quantity. Inventors concluded that prior art processes provide low yield due to misfolding and/or aggregation, which has been previously addressed to some extent using reverse phase chromatography and subsequent removal of organic solvent.

The presence of secretory, soluble but misfolded rhIL-11 has not been previously reported, as misfolded protein is generally believed to be aggregated intracellularly or salvaged for degradation (9). Methods of the inventive concept utilize the expression and purification of recombinant human IL-11 using a *Pichia pastoris* expression system and isolation from yeast fermentation medium without the use of reverse-phase chromatography.

Alternative approaches to the renaturation of rhIL-11 were explored, including use of chaotropes/denaturants such as urea, SDS, ammonium sulfate, and guanidine hydrochloride. Inventors determined that high concentrations of guanidine hydrochloride were capable of disrupting the interactions leading to self-aggregation of the rhIL-11, and allowed monomeric rhIL-11 to refold properly when concentration of the denaturant was reduced.

The process for the production of rhIL-11 from the culture medium begins with two-phase extraction to precipitate rhIL-11 from culture medium. Precipitation can be performed by any suitable means that provides selective or partially selective precipitation of rhIL-11 from the fermentation media, including introduction of salts (e.g. ammonium sulfate, sodium sulfate), organic solvents (e.g. methanol, ethanol, acetone, etc.), and/or hydrophilic polymers (e.g. dextran, dextrin, cyclodextrin, polyethylene glycol/PEG, etc.). For example, a final concentration of 8% (w/v) of PEG having a molecular weight of 8,000 Da (e.g. PEG-8000) can be used. Protein precipitated from the fermentation media is separated from the fermentation media for further processing. This separation can be accomplished by any suitable means, including settling, decanting, filtration, and/or centrifugal separation. In some embodiments the precipitated protein can be washed one or more times (for example, using a wash buffer containing the precipitating agent) prior to further processing.

Precipitated crude protein is subsequently dissolved in a buffer containing a denaturant, which can aid in disrupting protein aggregates. Suitable denaturants include chaotropic agents (e.g. urea, guanidine salts, isothiocyanate salts, etc.) and detergents (e.g. ionic detergents such as dodecyl sulfate salts, nonionic detergents such as TWEEN-20 and/or TWEEN-80, and zwitterionic detergents). For example, guanidine hydrochloride at a final concentration of 7M can be used to disrupt protein aggregates and re-solubilize precipitated protein.

Use of such denaturants, however, necessarily results in denaturation of the desired rhIL-11 product. This denaturation can be reversed to provide renatured/refolded rhIL-11 by removal of the denaturant or reducing the concentration of the denaturant. This removal can be rapid or gradual. Removal of the denaturant can be performed by any suitable means, including dilution (for example, with a buffer that contains either a reduced amount of denaturant or no denaturant and buffer exchange. Buffer exchange can be accomplished gradually (for example, by dialysis) or relatively rapidly (for example, by diafiltration, size exclusion chromatography, etc.). It should be appreciated that methods such as dialysis and diafiltration may be relatively ineffective in removing low-CMC detergents. In some embodiments direct dilution using a buffer that does not include surfactant can reduce denaturant concentrations sufficiently to permit refolding and renaturation of rhIL-11.

Surprisingly, Inventors have found that guanidine HCl is more effective than other chaotropic agents in providing both solubilization of precipitated rhIL-11 and subsequent renaturation into the active/native conformation on removal or reduction of the chaotrope. While guanidine HCl was found to be highly effective for this purpose, the Applicant considers that other chaotropic agents (such as urea, isothiocyanate salts, etc.) and/or detergents can be similarly effective under conditions optimized for their use.

It should be appreciated that correct refolding or renaturation of denatured rhIL-11 can be a function of factors other than denaturant concentration. For example, protein concentration during renaturation can impact the degree to which renaturation occurs and the formation of undesirable side products (such as dimers and higher order aggregates). While high protein concentration during renaturation are desirable from a process efficiency standpoint, such considerations must be balanced against the yield and purity of the final product. Protein concentration during renaturation or production of refolded rhIL-11 in methods of the inventive process can range from about 0.1 mg/ml to about 10 mg/mL. Surprisingly, Inventors have found that renaturation or production of refolded rhIL-11 provides optimal results at protein concentrations of less than 2 mg/mL. This can be conveniently achieved in combination with reducing the concentration of denaturant by dilution using a buffer that lacks denaturant.

Similarly, pH during a renaturation step can affect the refolding or renaturation of denatured rhIL-11. Inventors have found that renaturation can be carried out at a pH ranging from about 4 to about 12. In a preferred embodiment renaturation can be carried out at a pH ranging from about 7 to about 11. If necessary, pH can be adjusted by the addition of an acid (such as HCl) or base (such as NaOH) as appropriate, either before or during renaturation. Alternatively, pH can be adjusted by the addition of a buffering compound (such as a phosphate, a bicarbonate, Tris, HEPES, etc.) to the renaturation solution or by buffer exchange of the renaturation solution against a buffered solution of appropriate pH.

Following renaturation/refolding, rhIL-11 can be subjected to two chromatographic procedures. The first of these is ion exchange using a cation exchanger. Suitable cation exchangers include weak cation exchangers (for example, an ion exchanger carrying a carboxyl group) and strong cation exchangers (for example, an ion exchanger containing a sulfonic acid group). Such cation exchange can be performed using an ion exchange membrane, and ion exchange resin, and/or a phase-transfer solvent. In a preferred embodiment ion exchange is performed using a cation exchange resin packed in a chromatography column, which facilitates the collection of specific fractions. The rhIL-11 preparation can be applied at low ionic strength, permitting rhIL-11 to associate with or bind to the cation exchanger. After allowing unbound contaminants to pass rhIL-11 can be eluted or released from the cation exchanger by increasing the ionic strength of the applied buffer (for example, by increasing the concentration of NaCl or other salts) or by changing the pH of the applied buffer. Elution can be performed in a stepwise or gradient manner. It should be appreciated that high sample loads (in excess of 5 mg/mL) can be applied to some cation exchange columns, which can reduce losses due to nonspecific binding and increase process efficiency. For example, use of a CAPTO-S strong cation exchange column permits loading at 13 mg/mL and can provide active rhIL-11 at 40% to 60% step recovery.

In some embodiments a second chromatography step utilizing hydrophobic interaction chromatography is applied to the product of cation exchange in order to remove further contaminants and provide a more highly purified rhIL-11. Hydrophobic interaction chromatography can be performed using a membrane or a resin containing suitable hydrophobic moieties. Suitable hydrophobic moieties include propyl, butyl, hexyl, octyl, and phenyl groups. In some embodiments salts (such as sulfate or phosphate salts) can be added to the rhIL-11 solution prior to hydrophobic interaction chromatography. Such salts can be also serve to elute rhIL-11 from the cation exchanger in a previous ion exchange step. In a preferred embodiment hydrophobic interaction chromatography is performed using a hydrophobic interaction resin packed in a chromatography column, which facilitates collection of specific fractions during elution. The rhIL-11 can be eluted from such a hydrophobic interaction column by reducing the ionic strength of the applied buffer and/or increasing organic solvent and/or surfactant concentration of the applied buffer. This change in buffer composition can be a stepwise change or a can be applied as a gradient. It should be appreciated that rhIL-11 can be applied to such a hydrophobic interaction column at high protein loads, which can improve process efficiency. For example, a hydrophobic interaction chromatography column can be used at a 6-8 mg/mL sample load to provide an rhIL-11 product purity of greater than about 95% (through removal of oxidized rhIL-11 and other impurities) with a step yield of about 50%. The resulting purified rhIL-11 can then concentrated to at least 6 mg/mL and subjected to buffer exchange with 10 mM sodium phosphate pH 7 buffer for cold storage. Typical overall yield can be about 20-25%. The final purified bulk from such processes has been characterized in terms of identity, purity and potency; such characterization shows that the process is capable of yielding potent rhIL-11 at high purity.

The inventors noted that oxidation of rhIL-11 was a significant source of product contamination, with chromatography steps taken to reduce the presence of oxidized rhIL-11 having an impact on yield. Oxidation of recombinant protein mostly occurs during processing and storage, due to the presence of reactive oxygen species including superoxide ($O_2-$) and its protonated form (HOO.), hydrogen peroxide ($H_2O_2$), and other hydroxyl (OH.) (17). Protein oxidation of sulfur-containing residues notably plays a crucial role in stability. Oxidative stress of protein therapeutics in particular may lead to a variety of medical consequences including declined potency or elevated immunogenicity (18). Oxidative damage is often related to dissolved oxygen during fermentation, which is inevitable for aerobic fermentation. The inventors contemplate that modifications to the fermentation process can be undertaken to minimize generation of oxidized protein during culture, as well as optimization of downstream polishing processes for selective removal of oxidized protein.

It should be appreciated that the rhIL-11 preparation resulting from such methods is of high biological activity and high purity relative to rhIL-11 produced by prior art methods. When tested for biological activity using a 7TD1 cell line, polished rhIL-11 eluted from a hydrophobic interaction column as described above can have a biological activity ranging from about $4 \times 10^6$ U/mg protein to about $1.2 \times 10^7$ U/mg protein, and is typically about $6 \times 10^6$ U/mg protein. Purity of such an rhIL-11 preparation can be greater than 85%, greater than 90%, greater than 95%, greater than 98%, or greater than 99%. Typically, purity of rhIL-11 produced as described above in greater than 95%. As noted above, oxidized rhIL-11 is commonly found in products from aerobic fermentation. Preparations of rhIL-11 prepared as described above typically include 5% or less oxidized rhIL-11. Similarly, preparations of rhIL-11 prepared as described above can include less than 5%, less than 4%, less than 3%, less than 2%, less than 1%, or less than 0.5% dimeric rhIL-11 (i.e. rhIL-11 dimer) content. Typically such preparation include less than 1% dimeric rhIL-11 content.

EXAMPLES

Following are illustrative examples of the inventive concept, and should not be considered limiting.

Materials

The PICHIAPINK™ Expression System (#A11152, A11154) was acquired from Invitrogen Life Technologies. Restriction enzymes and polymerases for clone construction were purchased from FASTDIGEST enzymes of Thermo Fisher Scientific. Anti-foam 204 (#A6426), yeast nitrogen base without amino acid (#Y0626) were procured from Sigma-Aldrich. Reference standard of rhIL-11, derived from yeast was provided by Hangzhou Jiuyuan Gene Engineering Company (Lot #20121005/1006/1007/1008 & 20150402). Reagents and materials for immunoblotting, including 8-16% gradient SDS PAGE (#25268), STARTINGBLOCK Blocking Buffers (#37579), BLOCKER™ Casein (#37583), transfer buffer methanol free (#35045), TBS TWEEN 20 buffer (#28360) and 1-step ultra TMB (#37574), GIBCO® 2-mercaptoethanol (#21985-023) and the NOVEX Tris-Glycine 16% polyacrylamide gels (XP00162BOX) were purchased from Thermo scientific. Human IL-11 Affinity Purified Polyclonal Goat IgG (#AF-218-NA) and Donkey anti-goat IgG HRP affinity purified polyclonal (#HAF109) were procured from R&D systems. 7TD1 murine myeloma cell fused with C57Bl/6 spleen cell, was acquired from DSMZ (No. ACC 23). Trypsin of sequencing grade, modified from bovine pancreas (Cat. No. 11418025001) was purchased from Roche diagnostics. Mouse IL-11 receptor alpha (Cat. No. MBS553276) was acquired from MyBioSource, Inc. CELLTITER96® Aqueous Non-Radioactive Cell Proliferation Assay (MTS) (Cat. No. G5430) was purchased from Promega. RPMI 1640 (#SH30255.01), HI FBS (H #SH30071.03HI), STREP/PEN (HYCLONE, USA, SV30010) were purchased from HYCLONE, USA. The Purification resins-CAPTO S (Product code 17-5316-10), Capto Q (Product code 17-5441-01) and Butyl HP (Product code 17-5432-01) were procured from GE Healthcare Life Sciences. Trifluoroacetic acid (Cat. No. 302031) and acetonitrile (Cat. No. 34967) for HPLC operation were purchased from Sigma-Aldrich. Polyethylene glycol 8000 (#408050010), DL-methionine (#125652500) and guanidine hydrochloride (#364790025) were procured from Acros Organic. Ammonium sulfate (#11566) was acquired from Alfa Aesar. Phytone peptone (#210931) of non-animal origin was procured from Becton Dickinson.

Cloning and Cell Banking of rhIL-11 Expressing Yeast Clones

Recombinant human IL-11 gene was synthesized and cloned into pPINKα-HC yeast expression vector containing the gene encoding α-factor signal peptide, where the Glu-Ala repeats were deleted. The resulting recombinant vector was transformed into a protease deficient strain by electroporation for generation of stable clones. Approximately 40 clones from each transformation were picked and screened for high IL-11-expressing clones by visual inspection of expression intensity on SDS-PAGE, as visualized using Coomasie blue staining (data not shown). A western immunoblot using rhIL-11 specific antibody confirmed protein identity. The research master and working cell banks were prepared accordingly and stored in deep freeze.

To ensure consistent expression in quantity and quality, a cell master bank followed by a working cell bank was expanded after clonal purification by passage of 4 generations of the selected clone pPINKS2-IL11-24. The master and working cell banks were stored at −80° C. for long term storage.

High Density Fermentation

A one-liter fermentation system (BIOSTAT® B Bioreactor, Sartorius) was used for assessing the rhIL-11 expression level of the selected clone in high cell density culture using fed-batch fermentation. The fermentation was begun with inoculation of a 15-mL MGM (minimal glycerol medium; 0.2 µm filtered) medium lacking adenine with a thawed vial from the working cell bank. Composition of MGM was as follows:

1.34% Yeast nitrogen base without amino acid
1% glycerol
4 ppm biotin

After culturing in 30° C. with shaking at 250 rpm for 20 hours the resulting media was used to inoculate a 100-mL BSM (fermentation basal salts medium) with 0.5% phytone peptone (pH 5) for additional 48 hours. Compositions of BSM was prepared as follows:

Composition of BSM—

| | |
|---|---|
| Glycerol (50%) | 80 mL |
| Phosphoric acid (28%) | 26.7 mL |
| Calcium sulfate | 0.9 g |
| Magnesium sulfate | 14.9 g |
| Potassium hydroxide | 4.1 g |
| Potassium sulfate | 18.2 g |
| Phyton peptone | 5.0 g |
| PTM1 Trace salt | 4.4 mL |

Water was added to give a final volume of 1 L.

The pH of the broth was adjusted to 5.0, and filtered PTM1 trace salts were added slowly to avoid precipitation. PTM1 trace salts were prepared as follows:

Composition of PTM1 Trace Salts—

| | |
|---|---|
| Cupric sulfate-5$H_2$O | 6.0 g |
| Sodium iodide | 0.08 g |
| Manganese sulfate-$H_2$O | 3.0 g |
| Sodium molybdate-2$H_2$O | 0.2 g |
| Boric Acid | 0.02 g |
| Cobalt chloride | 0.5 g |
| Zinc chloride | 20.0 g |
| Ferrous sulfate-7H2O | 65.0 g |
| Biotin | 0.2 g |
| Sulfuric Acid | 5.0 mL |

Water was added to give a final volume of 1 L.

Next, 600 mL fermentation basal salts medium (BSM), containing 0.5% (w/v) soy phytone peptone was mixed with 500 µL anti-foam in a 1-L vessel, which was subsequently inoculated with the freshly cultured seed cells during glycerol batch phase under the same culturing conditions. The dissolved oxygen level—pO2 value was maintained at 80% by adjusting stirring speed, and air-inlet flow was set at 0.3 L/min. In the glycerol-fed batch phase 50% glycerol was fed to the vessel at a limiting rate of 6 mL/hr/L to boost growth. Cell density was monitored by measuring the OD 600 nm at different time points until OD reached about 180-200. During this phase, the pO2 value was maintained at no less than 30% by increasing stirring rate and air-inlet flow. The expression of rhIL-11 was induced in methanol-fed batch by feeding 30% (v/v) methanol at 5.5 mL/hr/L for initial 4-5 hours, followed by 50% (v/v) methanol at 5.5-9 mL/hr/L. The pO2 value was maintained at no less than 20% by increasing stirring rate and air-inlet flow. The medium was harvested after induction for 48-72 hours.

Expression Level of the rhIL-11 Expression Clone

The protein content of media at desired expression levels was determined by visual inspection against intensities of reference standards on the same SDS-PAGE gel, as the value was found to be consistently underestimated by ELISA due to presence of misfolded IL-11 (which was found to be largely undetected by antibodies). Alternatively, protein content could be quantified using densitometry software (such as GELQUANT.NET (version 1.8.2) provided by BiochemLab Solutions). Accurate quantitation of expression levels was also achieved using RP-HPLC. Secretory rhIL-11 in medium was precipitated by adding 8% (w/v) PEG-8000 and collected after centrifugation. The pellet was resuspended in pH 8 sodium phosphate buffer containing 7 M guanidine hydrochloride. After removing the insoluble particulate by centrifugation, the expression productivity was calculated by comparing integrated area against a reference standard of a known concentration using the following chromatographic procedures for RP-HPLC operation:

Column: PLRP-S column (Agilent), 8 µm, 2.1×150 mm, 300 Å pore size, equipped with a guard cartridge
Mobile phase A: 0.1% (v/v) TFA in water; Mobile phase B: 0.1% (v/v) TFA in 90% (v/v) acetonitrile
Flow rate: 0.2 ml/min.
Detection: 215 nm.
Inj. Vol. 5-10 µl.
Gradient: A typical solvent gradient is shown in Table 1.

TABLE 1

| Time (min) | A % | B % |
|---|---|---|
| 0 | 100 | 0 |
| 1 | 100 | 0 |
| 2 | 70 | 30 |
| 33 | 25 | 75 |
| 33.1 | 10 | 90 |
| 35 | 10 | 90 |
| 35.1 | 100 | 0 |
| 50 | 100 | 0 |

Protein Concentration of Purified rhIL-11

The concentration of rhIL-11 following chromatographic steps was determined by UV absorbance at 280 nm, using UV/Vis microplate and cuvette spectrophotometer (e.g. a MULTISKAN GO from Thermo Scientific). An extinction coefficient (Ec) in units of $M^{-1}$ $cm^{-1}$, at 280 nm measured in water was calculated to be 17,990 using the following formula:

$$Ec = Number(Tyr) \times 1490 + Number(Trp) \times 5500 + Number(Cys) \times 125$$

The protein concentration in unit of molar is calculated as follows:

$$Concentration = (Absorbance\ at\ 280\ nm)/Ec$$

Alternatively, protein concentration can be directly determined by ultraviolet spectroscopy at 280 nm, using an absorbency value of 0.944 for a 0.1% (i.e. 1 mg/ml) solution. Protein quantitation using absorbance at 280 nm measures the absorbance of aromatic amino acids such as tryptophan and tyrosine, and does not detect the presence of a PEG moiety. As a result, protein concentration by weight stated herein excludes the presence of PEG molecules. Both values can be calculated by the ProtParam, a tool to calculate physical and chemical parameters for a given protein (10).

Sodium Dodecyl Sulfate-Polyacrylamide gel electrophoresis, staining and immunoblotting The apparent molecular weight of protein was evaluated by Sodium Dodecyl Sulfate-Polyacrylamide gel electrophoresis (SDS-PAGE) with Biorad's MINI-PROTEAN system coupled with pre-cast gels. The resulting polyacrylamide gels were visualized following Coomasie blue or silver staining.

Protein immunoblotting was performed with Mini Trans-Blot Cell acquired from Bio-Rad. Following protein electrophoresis, the proteins resolved on the SDS-PAGE were transferred to a nitrocellulose membrane using a 300 mA current for one hour. The nitrocellulose membrane was subsequently blocked using a blocking buffer for 30 minute to overnight, followed by washing with TBS-TWEEN 20 buffer 6 times, 5 minutes each. Protein of interest was detected on the membrane by incubation with a casein-blocked diluted (1:2,000) primary antibody (goat IgG) against human IL-11 for one hour at room temperature. After washing the membrane with TBS-TWEEN 20 buffer 6 times, 4 mins each, the membrane was incubated with a casein-blocked diluted (1:3,000) secondary antibody against goat IgG for an hour at room temperature. The membrane was transferred to a shallow tray and incubated with 1-step ULTRA TMB according to manufacturer's procedures. The process of color development was monitored carefully and was washed briefly in water when bands of the desired intensity were achieved.

Purification of rhIL-11

Aqueous two-phase extraction: Soluble but misfolded rhIL-11 was precipitated from fermentation medium by a aqueous two-phase extraction. Solid PEG 8000 was added directly to a filtrate of fermentation medium to give a final concentration of 6% to 8% (w/v). The solid polymer was dissolved completely by gentle stirring, followed by centrifugation at 4,000 rpm for 10 min to recover precipitated proteins.

Refolding rhIL-11: The precipitated protein was dissolved in 20 mM sodium phosphate containing 7 M guanidine hydrochloride (GdHCl) pH 8-9 buffer solution to a final concentration of 2 mg/mL and incubated at room temperature for an hour. An 11-fold volume of 4 mM sodium phosphate buffer pH 8 was added to dilute the GdHCl, allowing the denatured protein to undergo proper refolding by incubating the solution at room temperature for 2 hours. Prior to subjecting to ion-exchange chromatography, the resulting solution was diluted by simple dilution or buffer exchange using ultrafiltration or dialysis, with 4 mM phosphate buffer to obtain a conductivity less than 6.5 mS/cm.

Cation-exchange chromatography: Ion exchange chromatography was carried out using a commercial chromatography apparatus (e.g. the AKTAPRIME PLUS from GE Healthcare Life Sciences). Prior to loading onto chromatographic column, the resulting diluted solution was centrifuged or filtered through a 0.45 or 0.2 µm membrane to remove particulates. The mixture was loaded onto a CAPTO S column that was equilibrated with buffer A containing 20 mM sodium phosphate pH 8. The protein was eluted with a gradient- or a step-elution of buffer B, containing 20 mM sodium phosphate pH 8 and 1M NaCl.

Hydrophobic-interaction chromatography: Hydrophobic interaction chromatography was carried out using a commercial chromatography apparatus (e.g. the ÄKTAprime plus from GE Healthcare Life Sciences). Fractions containing rhIL-11 from the cation-exchanger (CAPTO S) were pooled and added to 0.5 M ammonium sulfate with 5 mM DL-methionine. The resulting diluted solution was centrifuged or filtered through a 0.45 or 0.2 µm membrane to remove particulates prior to sample loading. The mixture was loaded onto a Butyl HP column that was equilibrated with buffer A containing 0.5 M ammonium sulfate and 5 mM DL-methionine in 10 mM sodium phosphate pH 7 buffer solution. The protein was eluted with a step- or gradient-elution of buffer B, containing 10 mM sodium phosphate pH 7 buffer. Additional 0.2 M acetic acid was employed to elute tightly bound rhIL-11.

Purity determined by size-exclusion chromatography: The content of covalently and non-covalently aggregated rhIL-11 in addition to other high molecular weight species, were analyzed by size-exclusion chromatography (SEC) employing a commercial UPLC system provided with a diode-array detector (e.g. the UltiMate 3000 Rapid Separation LC Systems from Thermo Scientific). The chromatographic procedure was carried out using:

Column: Waters Acquity BEH200 SEC 1.7 µm, 4.6×150 mm, 300 Å pore size (Part #186005225), equipped with a guard cartridge (Part #186005793).
Mobile phase: 25 mM sodium phosphate pH 7.0 containing 0.5 M NaCl
Flow rate: 0.3 ml/min.
Detection: 280 nm.
Stop time: 10 min.
Injection of 5 µg of protein Purity and molecular mass determined by LC/MS: The purity of rhIL-11 was analyzed by reverse-phase (RP) chromatography employing (a) an UPLC provided with a diode-array detector (e.g. the UltiMate 3000 Rapid Separation LC Systems from Thermo Scientific, or the Agilent 1290 infinity UPLC system) coupled to an Agilent 6540 UHD Accurate Mass Q-TOF LC/MS system. The chromatographic procedure was carried out using procedures as follows:

Column: ACQUITY UPLC PST C18 Column, 300 Å pore size, 1.7 µm, 2.1 mm×150 mm (Part No. 186003687), equipped with the Acquity BEH C18 VanGuard Pre-column, 300 Å pore size, 1.7 µm, 2.1×5 mm. (Part No. 186004629).
Mobile phases and gradient: Mobile phase A: 0.1% (v/v) trifluoroacetic acid (TFA) in water; Mobile phase B: 0.1% (v/v) TFA in 95% (v/v) acetonitrile
Flow rate: 0.4 ml/min.
Column temperature: ambient.
Detection: 214 nm.
Injection: 5 µg.

Gradient—A typical solvent gradient is shown in Table 2.

TABLE 2

| Time (min) | A % | B % |
| --- | --- | --- |
| 0 | 100 | 0 |
| 1 | 100 | 0 |
| 2 | 70 | 30 |
| 21 | 25 | 75 |
| 21.1 | 10 | 90 |
| 23 | 10 | 90 |
| 23.1 | 100 | 0 |
| 30 | 100 | 0 |

Operation parameters of mass spectrometry were as followed m/z range and polarity: 150-3000 positive
Source parameters: Gas temperature 300° C.; Gas flow 8 l/min
Nebulizer 35 psig
Sheath gas temperature 380° C.; Sheath gas flow 11 l/min
Scan source parameters:
VCap=3500
  Nozzle voltage 1,000V
  Fragmentor 175
  Skimmer1 65
  OctopoleRFPeak 750

Cell-Based Bioassay

The biological activity of rhIL-11 was calculated in a cell proliferation assay, using 7TD1 cell-line. IL-11 reference standard and unknown samples were sterilely diluted to provide a concentration range of 20,000 ng/ml to 0.2 pg/ml by 10 fold (total 9 dilutions). 50 µl of rhIL-11 standard or sample were added to wells (e.g. wells of a 96-well plate) containing 7TD1 cells at 4,000 cells per well, in duplicate. Cells were incubated at 37° C. in a humidified atmosphere containing 5% $CO_2$ to characterize their response to different IL-11 concentrations in the presence of 2 µg/mL IL-11 receptor for three days (12). For the cell proliferation assay, 20 µl per well of MTS solution was dispensed into the wells using a multichannel pipette and incubated in the 37° C. incubator for 2.5-3 hours, depending on the signal development. After incubation, the plate was read for absorbance at 490 nm using a UV/Vis microplate and cuvette spectrophotometer (e.g. a MULTISKAN GO from Thermo Scientific).

The EC50 (half maximal effective concentration) of dose response curve is determined by plotting the absorbance of 490 nm on the y-axis against concentrations on the x-axis, by fitting sigmoid dose-response curves with GraphPad software Prism 6, against the four-parameter non-linear logistic equation:

$$y=((a-d)/(1+(x/c)b))+d$$

where:
a is the y-axis of minimum asymptote as the concentration approaches zero; b is the slope referring to the steepness of the curve
c is the $EC_{50}$
d is y-axis of maximum asymptote as the concentration approaches infinite
x is the concentration
y is the absorbance at 490 nm.

The specific bioactivity is derived from the following equation:

Specific activity (U/mg)=(Specific activity of reference)×($EC_{50}$ reference/$EC_{50}$ sample)

Characterization of Secondary Structure by Circular Dichroism

Far-UV circular dichroism (CD) spectra were recorded using a Jasco J-815 spectropolarimeter using a quartz cell of 1.0 cm path length at room temperature. Protein samples were diluted to about 0.02 mg/mL using deionized water or 5 mM sodium phosphate pH 7. Secondary structure was monitored in the far-UV region (190 nm to 250 nm) using operational parameters including scanning rate, bandwidth and response set at 100 nm/min, 1 nm and 2 sec respectively. Spectra were obtained from an average of 3 scans.

Peptide Mapping

A proteolytic solution was prepared in 50 mM sodium phosphate pH 8 buffer containing 2 mg/mL protein by adding 1/100 (w/w) trypsin of sequencing grade. After incubation at room temperature for 6 hours, TFA (or formic acid) was introduced to obtain final concentration of 0.1% to quench the reaction. Precipitate was removed by centrifugation or filtration through a 0.2 or 0.4 µm membrane prior to injection. Peptide identification was carried out with the LC/MS system—Agilent 1290 infinity UPLC system coupled with Agilent 6540 UHD Accurate Mass Q-TOF LC/MS system. The chromatographic procedure was carried out as follows:

Column: ZORBAX 300 SB-C8, 2.1×150 mm, 5 µm, 300 Å pore size (Agilent Part No. 883750-906).
Mobile phases and gradient: Mobile phase A: 0.1% (v/v) TFA in water; Mobile phase B: 0.1% (v/v) TFA in 95% (v/v) acetonitrile
Flow rate: 0.2 ml/min.
Detection: 214 nm.
Injection: 10 µg.

Gradient—A typical solvent gradient is shown in Table 3.

TABLE 3

| Time (min) | A % | B % |
|---|---|---|
| 0 | 100 | 0 |
| 3 | 100 | 0 |
| 8 | 95 | 5 |
| 45 | 55 | 45 |
| 45.1 | 0 | 100 |
| 52 | 0 | 100 |
| 52.1 | 100 | 0 |
| 65 | 100 | 0 |

Operation parameters of mass spectrometry were as follows:
m/z range and polarity: 400-1700 positive;
Source parameters:
Gas temperature 300° C.
Gas flow 8 l/min
Nebulizer 35 psig
Sheath gas temperature 350° C.
Sheath gas flow 11 l/min
Scan source parameters:
VCap=3500
Nozzle voltage 1,000V
Fragmentor 175
Skimmer 165
Collision Energy:

| Charge | Slop | Offset |
|---|---|---|
| 2 | 4 | 1 |
| 3 | 3.5 | −2 |
| >3 | 3.2 | −4.8 |
| 1 | 0 | 20 |

The estimated molecular masses of proteolytic peptides cleaved by trypsin are listed in Table 1. Identification of each proteolytic peptide was performed manually with the MS Product tool, which generates possible fragment ions resulting from fragmentation of a peptide in m/z spectra. Resulting tryptic peptides from recombinant IL-11 are shown in Table 4.

TABLE 4

| Monoisotopic Mass | Amino acid Position | Peptide No. | Amino acid sequence | SEQ ID NO. |
|---|---|---|---|---|
| 773.4 | 1-8 | T1 | GPPPGPPR | SEQ ID NO. 1 |
| 669.3 | 9-14 | T2 | VSPDPR | SEQ ID NO. 2 |

TABLE 4 -continued

| Monoisotopic Mass | Amino acid Position | Peptide No. | Amino acid sequence | SEQ ID NO. |
|---|---|---|---|---|
| 1216.6 | 15-25 | T3 | AELDSTVLLTR | SEQ ID NO. 3 |
| 774.4 | 26-32 | T4 | SLLADTR | SEQ ID NO. 4 |
| 798.5 | 33-39 | T5 | QLAAQLR | SEQ ID NO. 5 |
| 261.1 | 40-41 | T6 | DK | N/A |
| 3317.7 | 42-74 | T7 | FPADGDHNLDSLPTLAMSAG | SEQ ID NO. 6 |
| 287.2 | 75-76 | T8 | LR | N/A |
| 949.5 | 77-84 | T9 | ADLLSYLR | SEQ ID NO. 7 |
| 837.5 | 85-90 | T10 | HVQWLR | SEQ ID NO. 8 |
| 174.1 | 91-91 | T11 | R | N/A |
| 618.3 | 92-98 | T12 | AGGSSLK | SEQ ID NO. 9 |
| 1326.7 | 99-110 | T13 | TLEPELGTLQAR | SEQ ID NO. 10 |
| 402.2 | 111-113 | T14 | LDR | N/A |
| 400.3 | 114-116 | T15 | LLR | N/A |
| 174.1 | 117-117 | T16 | R | N/A |
| 859.5 | 118-124 | T17 | LQLLMSR | SEQ ID NO. 11 |
| 2598.4 | 125-150 | T18 | LALPQPPPDPPAPPLAPPSSAWGGIR | SEQ ID NO. 12 |
| 1913.1 | 151-168 | T19 | AAHAILGGLHLTLDWAVR | SEQ ID NO. 13 |
| 655.5 | 169-174 | T20 | GLLLLK | SEQ ID NO. 14 |
| 275.2 | 175-176 | T21 | TR | N/A |
| 131.1 | 177-177 | T22 | L | N/A |

Amino Acid Composition

Amino acid composition was determined using a Hitachi High-Speed Amino acid Analyzer L-8900, which provides separation of hydrolyzed amino acid by ion-exchange mechanism followed by derivatization with ninhydrin. Prior to hydrolysis protein samples were prepared at 1 mg/mL in triplicate and hydrolyzed under nitrogen in the condition of 6N HCl, 110° C. for 22 hours. The hydrolyzed sample was resuspended in 0.02 N HCl following evaporation in 80° C. water bath. Under such acidic hydrolysis conditions asparagine and glutamine are deamidated to form their respective acids. Tryptophan is completely degraded. Cysteine and methionine are oxidized and are not readily detected from the acid hydrolysate. Tyrosine, serine and threonine are partially hydrolyzed (13).

High Cell Density Fermentation

Figure 1B:
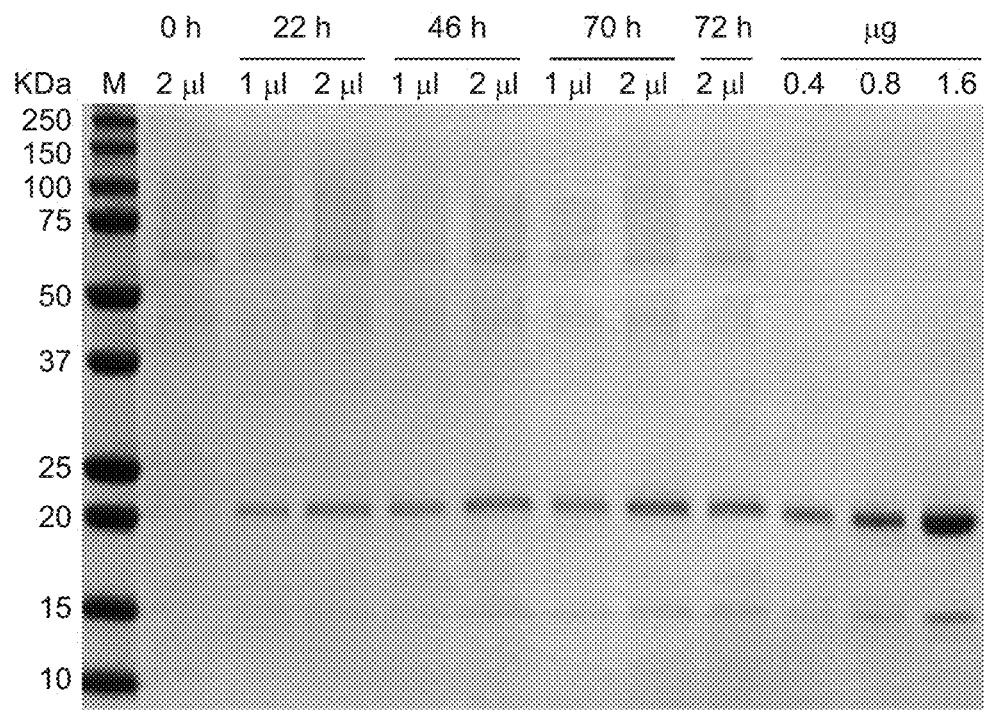
Figure 1C:
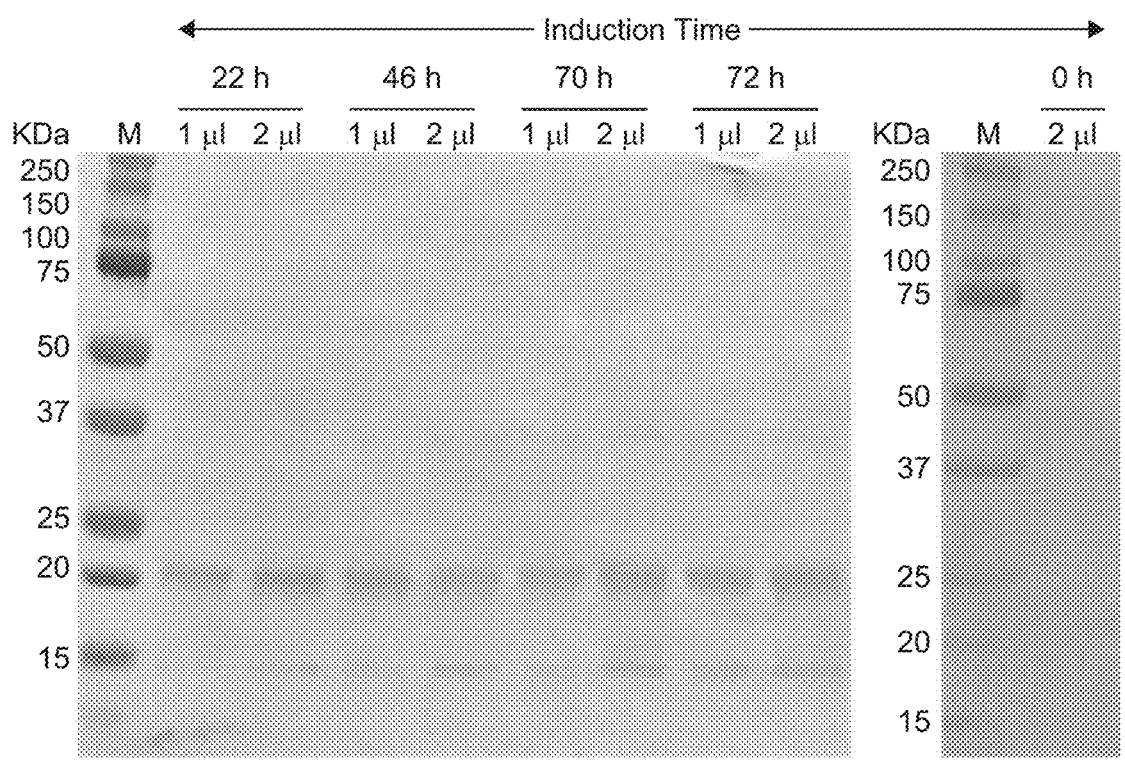

Glycerol-fed batch fermentation was carried out in a 1-L fermentor inoculated with the protease deficient strain (pPINKS1-IL11-24) thawed from a vial of the research working cell bank for downstream purification development. A typical cell growth curve is illustrated in FIG. 1A, showing the cell culture achieving 200 OD after additional feeding of glycerol. The cell density continued to grow up to 250 OD after methanol induction, but gradually declined after 22 hours post induction, probably due to insufficient nutrient. Samples of fermentation broth were taken at 22-hr, 46-hr and 70-hr post induction time points and were analyzed by non-reducing SDS-PAGE. FIG. 1B and FIG. 1C show typical results of SDS-PAGE and immunoblotting respectively. Expression level was not determined by ELISA as this method was found to consistently underestimate productivity. Instead the productivity of rhIL-11 was estimated by the intensities of Coomasie blue staining relative to those of a reference standard, by either visual inspection or densitometry, and found to yield approximately 0.4-0.6 g/L. In the SDS-PAGE developed by Coomasie blue staining there were some obvious bands below the position of rhIL-11 (approximately 20 KD) at about 15 KD (FIG. 1B), which were degraded species as verified by immunoblotting using antibodies against rhIL-11 (FIG. 1C). An expression productivity of fermentation medium determined by RP-HPLC was about 0.4 mg/mL.

Capturing IL-11 Using Cation-Exchange Chromatograph

Given the high isoelectric point of IL-11 (pI=11), cation-exchange chromatography was attempted to capture the rhIL-11 from fermentation medium at pH 8. After removing cell paste by centrifugation, a few hundred milliliter broth was subjected to buffer-exchange by ultrafiltration or was directly diluted with at least 10-volume water to give a conductivity of less than 3 mS/cm. To recover rhIL-11 a small amount of solution, equivalent to about 2 milligrams of rhIL-11, was loaded onto a 1 mL CAPTO-S column (a cation exchanger) that was previously equilibrated with 20 mM Tris pH 8 buffer. Bound protein was eluted with NaCl gradient up to 1 M NaCl. Results of SDS-PAGE and immunoblotting indicated that rhIL-11 was found in the flow-through fractions and did not bind to the column (data not shown). To ensure the suitability of the purification system using the cation exchanger, 0.5 mg of reference rhIL-11 was spiked in the 1 mL fermentation broth as a positive control, followed by the purification procedures aforementioned. The recovery of about 30% suggested the suitability of the cation exchanger for isolating rhIL-11 as it was successfully eluted by NaCl gradient in the same manner. Isolation was attempted with an anion-exchanger (CAPTO-Q) by recovery of flow-through material. A small amount of solution, equivalent to about 2 milligrams of rhIL-11, was loaded onto a 1 mL CAPTO-Q column (anion exchanger) to recover rhIL-11 in the flow-through. The column was previously equilibrated with 20 mM Tris pH 8 buffer, followed by elution with NaCl gradient up to 1 M NaCl. Surprisingly, results of SDS-PAGE indicated successful recovery of rhIL-11 in the NaCl-containing fractions but not in the flow-through (data not shown). This purification process was repeated leading to consistent and reproducible results, affirming the unexpected ionic characteristic of expressed rhIL-11.

The inventors noted weak bioactivity of the rhIL-11 in the cell-based proliferation assay and an underestimation of rhIL-11 content using ELISA quantitation when using samples of fermentation medium. Interestingly the bioactivity was restored when the fermentation broth was spiked with reference rhIL-11 (data not shown). Inventors concluded that unexpected binding (or lack thereof) on the ion-exchangers and loss of bioactivity indicated altered physical properties of the expressed protein.

Liquid Two-Phase Extraction

Figure 2:
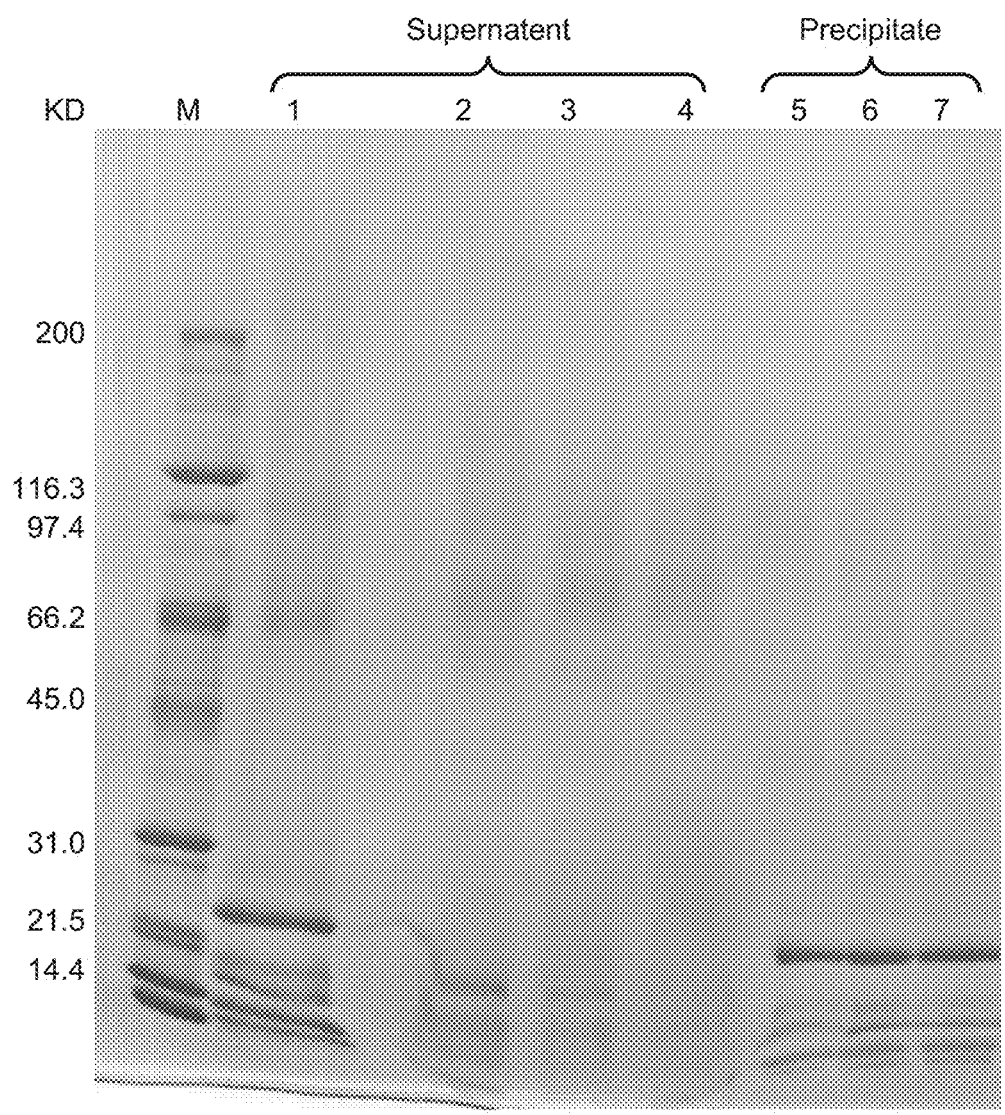
FIG. 2 shows a typical non-reducing 16% SDS-PAGE gel illustrating the recovery of rhIL-11 after the aqueous two-phase extraction.

Prior to further investigation, the expressed protein was recovered from fermentation medium by a simple aqueous two-phase extraction. The extraction was developed to precipitate non-native rhIL-11 from liquid phase, by adding polyethylene glycol 8000. Solid PEG-8000 was added to one mL of filtered fermentation broth to obtain 2.9, 3.8, 5.0, 6.2, 7.3, and 8.2% (w/v) respectively. After incubating at 4° C. for an hour, cloudiness was only visualized in samples containing 6.2, 7.3 and 8.2% PEG 8000. Precipitates were collected by centrifugation using a desktop centrifuge at top speed for 5 minutes and the precipitated proteins were reconstituted with 1-mL of sodium phosphate buffer at pH 8. As shown in FIG. 2, nearly all the rhIL-11 could be recovered from the precipitate by adding PEG 8000 as little as 6% (w/v). In subsequent studies, rhIL-11 was recovered from the culture medium by precipitation with PEG unless otherwise stated.

Structural Characteristics of Secreted rhIL-11 in Fermentation Medium

Figure 3:
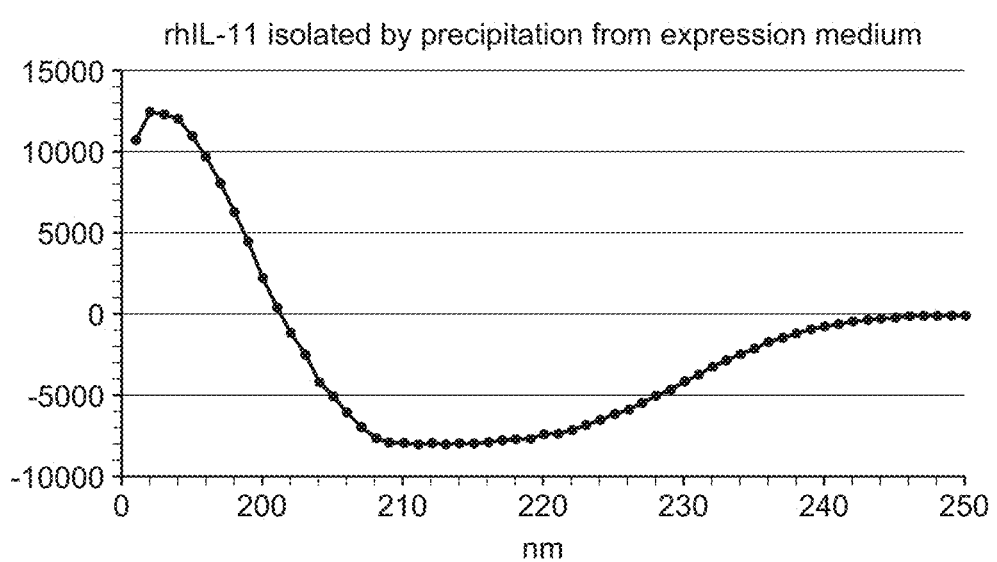
FIG. 3 provides a far-UV CD Spectrum of crude rhIL-11 isolated from expression medium using a liquid two-phase extraction.

The structural characteristics were studied using Circular Dichroism (CD) and size-exclusion chromatography. Precipitated rhIL-11 recovered from the liquid two-phase extraction by adding PEG 8000 at 8% into fermentation medium was resuspended in deionized water at about 0.02 mg/mL. A typical CD spectrum is shown in FIG. 3, revealing significant helical structure (as shown by negative bands at ~222 nm and 210 nm, and a positive band at ~195 nm). This suggests that the crude rhIL-11 maintained helical backbones.

Figure 4:
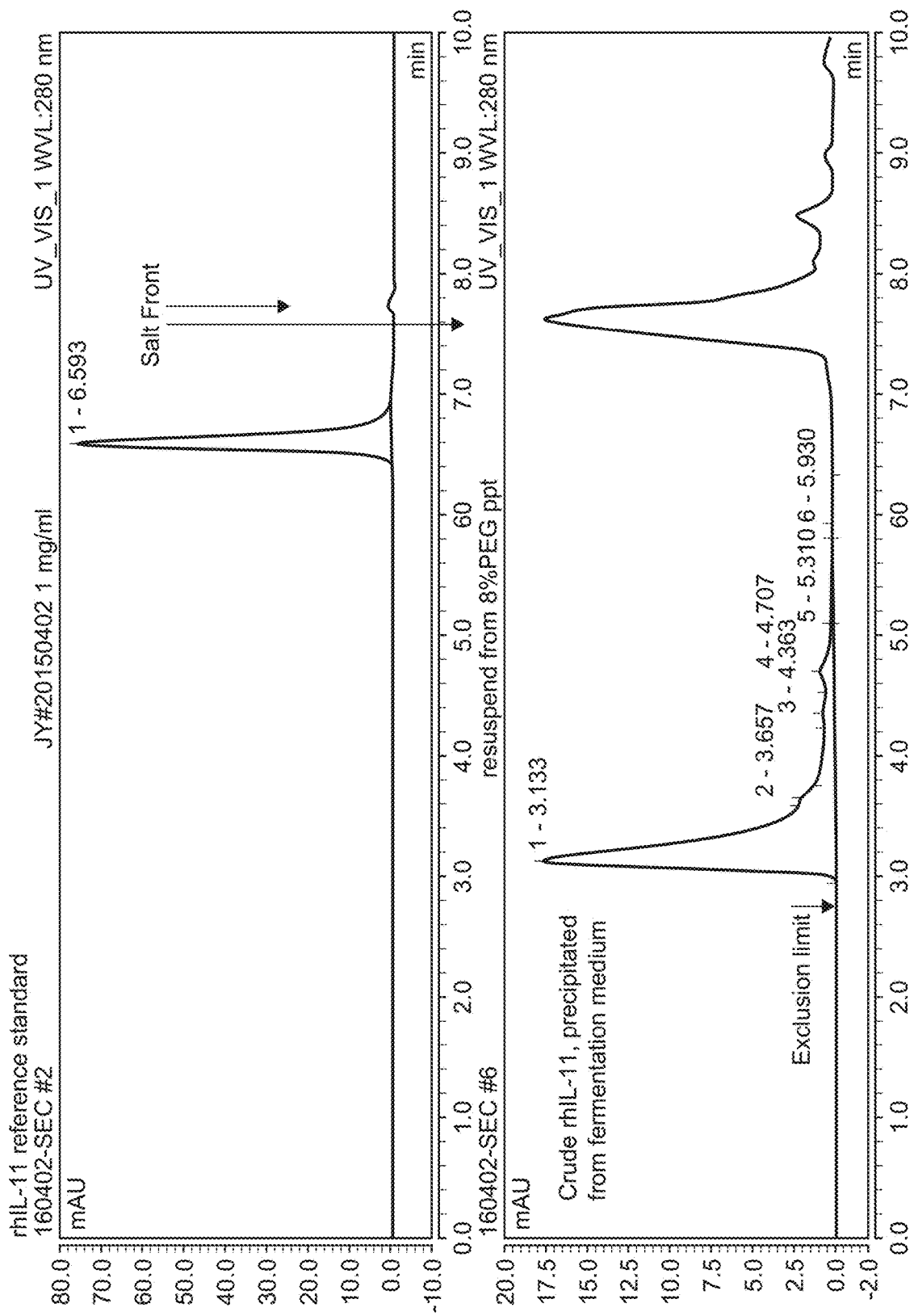
FIG. 4 shows the results of size-exclusion chromatography of rhIL-11 precipitated from fermentation medium (lower panel) and a reference standard of rhIL-11 (upper panel).

For size exclusion studies PEG-precipitated protein was resuspended in 20 mM sodium phosphate pH 7 buffer to a concentration of about 1 mg/mL. The molecular size was compared with a reference standard of rhIL-11 using an Acquity BEH200 SEC column, capable of separating globular proteins ranging from 10K to 450K Da. The results as seen in FIG. 4 indicate that crude rhIL-11 from fermentation medium has an unexpectedly high molecular mass. This suggests that secreted rhIL-11 is present as soluble aggregates in the culture broth. In combination with the CD data it is contemplated that the helical structure of the secreted rhIL-11 is maintained, but that the monomeric molecules tend to associate non-covalently with one another to form intermolecular helical bundles. Inventors believe, without being bound to theory, that this is a cause of low yield in the original process, resulting in changes in physicochemical characteristic and loss of bioactivity.

Figure 5:
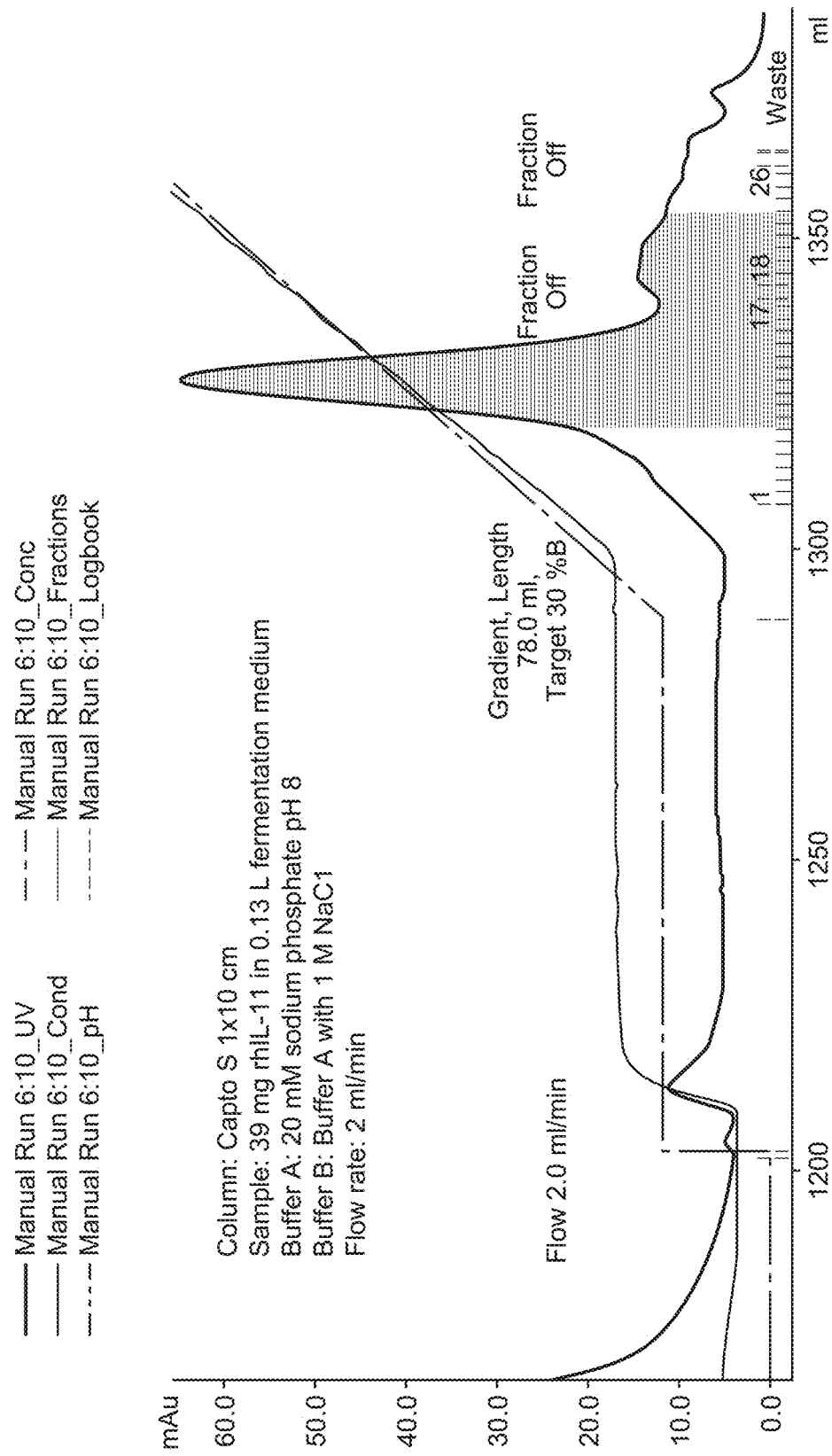
FIG. 5 shows results from isolation of rhIL-11 from a fermentation medium containing 0.1% TWEEN-80 by liquid chromatography using a CAPTO-S column (a cation exchanger). The red trace depicts in-line conductivity; and the blue trace depicts UV absorbance at 280 nm. The shaded region represents fractions judged suitable for pooling.

Prevention of Self-Aggregation Using Non-Ionic Surfactant in Fermentation Medium Although *Pichia pastoris* expresses protein through eukaryotic folding pathways, self-aggregation and misfolded secretory rhIL-11 in high-density yeast culture has not been previously documented. The aggregated form creates significant problems such as loss of bioactivity and poor yields in downstream purification steps. One strategy of preventing aggregation is to introduce additives or surfactants in fermentation medium (14). To investigate this TWEEN-80 at 0.1% was introduced in a 1-L high-density fed-batch fermentation medium. After harvest, 130 mL fermentation medium was added with 10×water to reduce conductivity. After removing particulate matters by simple filtration through a 0.45 or 0.2 μm membrane, the resulting solution was charged onto a cation-exchanger (CAPTO-S) in order to recover bioactive rhIL-11. A typical purification profile is shown in FIG. 5. After loading onto the column, the column was washed by 50 mM NaCl buffer, followed by 50-300 mM NaCl gradient over 10 column volume. Fractions containing rhIL-11 were combined as determined by SDS-PAGE analysis of selected fractions, resulting in a step yield at 13.6%. The finding suggested 0.1% TWEEN-80 could reduce self-aggregation during fermentation to some extent, however the recovery of bioactive rhIL-11 may not be satisfactory.

Refolding Optimization for rhIL-11 Renaturation

Figure 6:
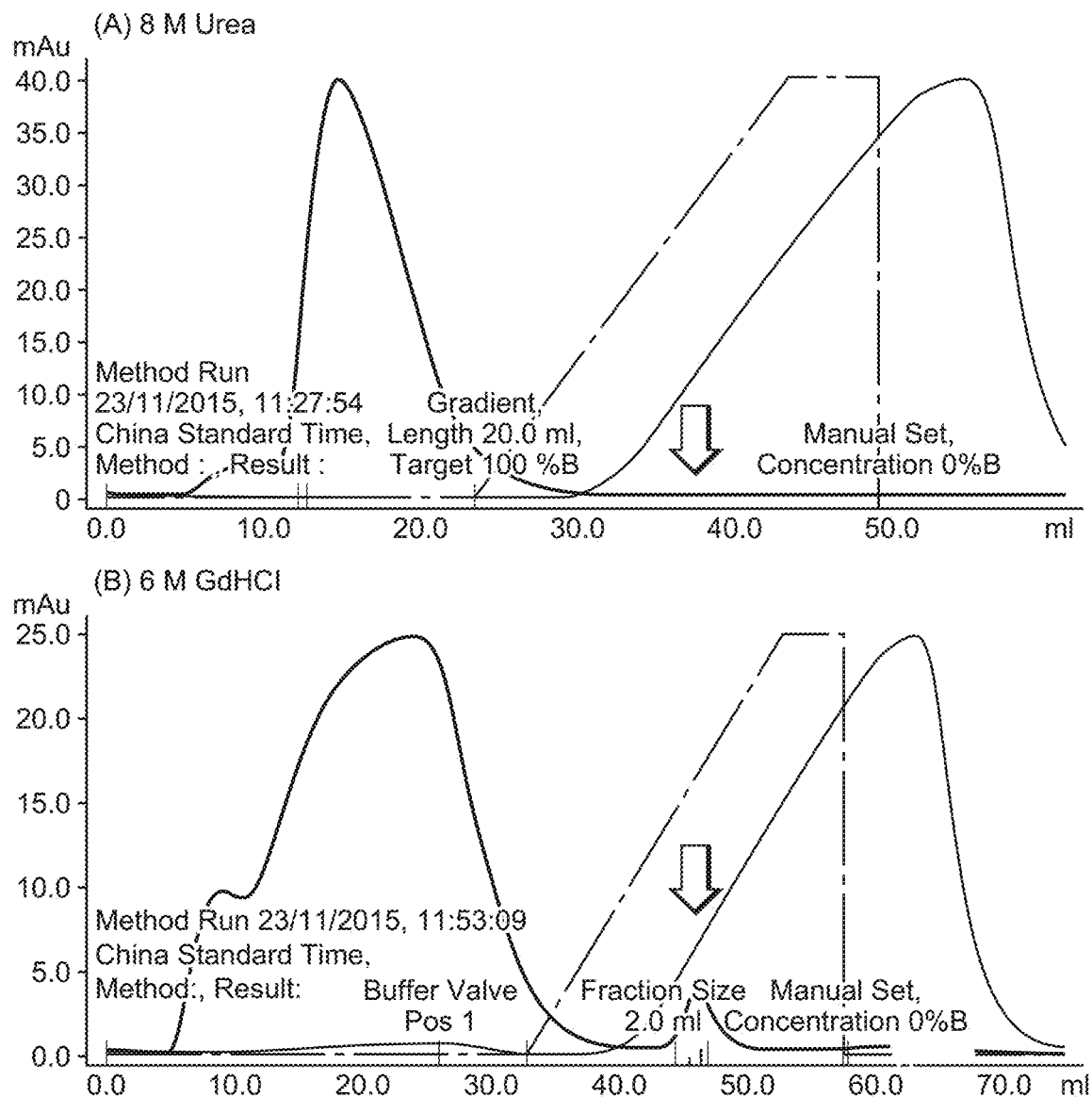
FIGS. 6A and 6B show results of isolation of rhIL-11 on a CAPTO-S cation exchanger after refolding in the presence of denaturants.

Refolding of protein in solution is a result of a number of physiochemical factors including ionic strength, pH, temperature, protein concentration and so on. Urea, ammonium sulfate, SDS and guanidine hydrochloride (GdHCl), were studied as denaturants that could be useful in a refolding process for rhIL-11. Protein precipitated from 2 mL fermentation medium after PEG precipitation was reconstituted at 5 mg/mL with respective denaturant-containing buffer solution: 8 M urea, 1 M ammonium sulfate, 0.5% SDS or 6 M GdHCl. After dilution with water to achieve a conductivity of less than 5 mS/cm, only the native and biologically active rhIL-11 is adsorbed onto a cation-exchanger and expected to be eluted by NaCl salt gradient. Results indicated that with the exception of 6 M GdHCl, denaturants failed to renature rhIL-11, as seen in FIG. 6 (which shows that rhIL-11 from the refolding solution containing 6M GdHCl was eluted successfully using a NaCl gradient). In other studies protein precipitated from 2 mL fermentation after PEG precipitation was dissolved in 2 mL alkaline solution consisted of 0.1 N NaOH, 0.1 N NaOH with 70% ethanol, or 0.1 N NaOH with 1% TWEEN 20. After dilution with water and pH adjustment to pH 8 the cation-exchanger recovered little native rhIL-11 from such solutions. Results suggest that in preferred embodiments of the inventive concept guanidine hydrochloride can be used to successfully renature rhIL-11 at high yield.

Figure 7:
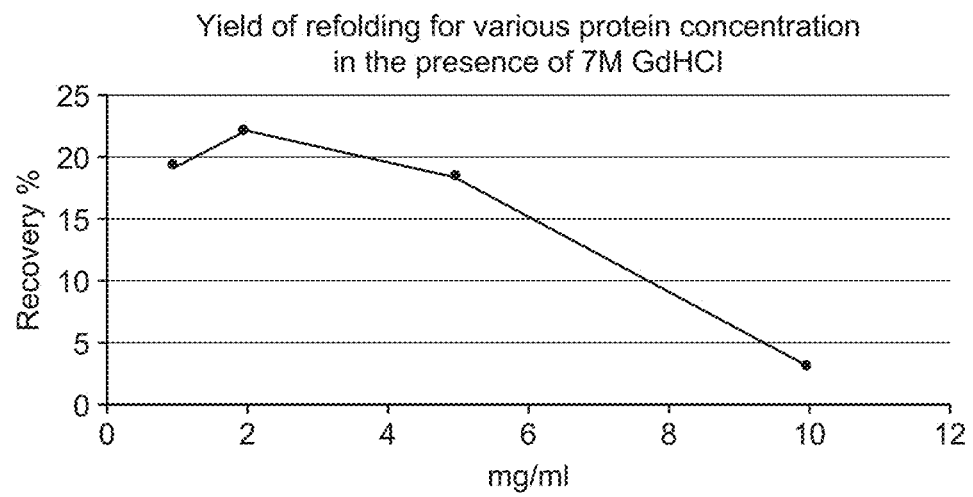
FIG. 7: Refolding yield by dissolving precipitated protein in various concentration in the presence of 7M GdHCl

Protein concentration used in the refolding process was optimized by dissolving the PEG protein precipitate at various protein concentrations in a 7M GdHCl solution. Protein from 2 mL fermentation medium was collected after PEG precipitation and was reconstituted at various protein concentrations in 7 M GdHCl buffer solution. After refolding by simple dilution, refolded rhIL-11 of each preparation was isolated with a cation exchanger as described above. The yield of refolding was evaluated by comparing observed peak area to that of a reference standard of rhIL-11, as shown in FIG. 7. Results indicate that refolding occurred at all concentrations tested, with a broad yield optimum at about 2 mg/mL protein concentration.

Figure 8:
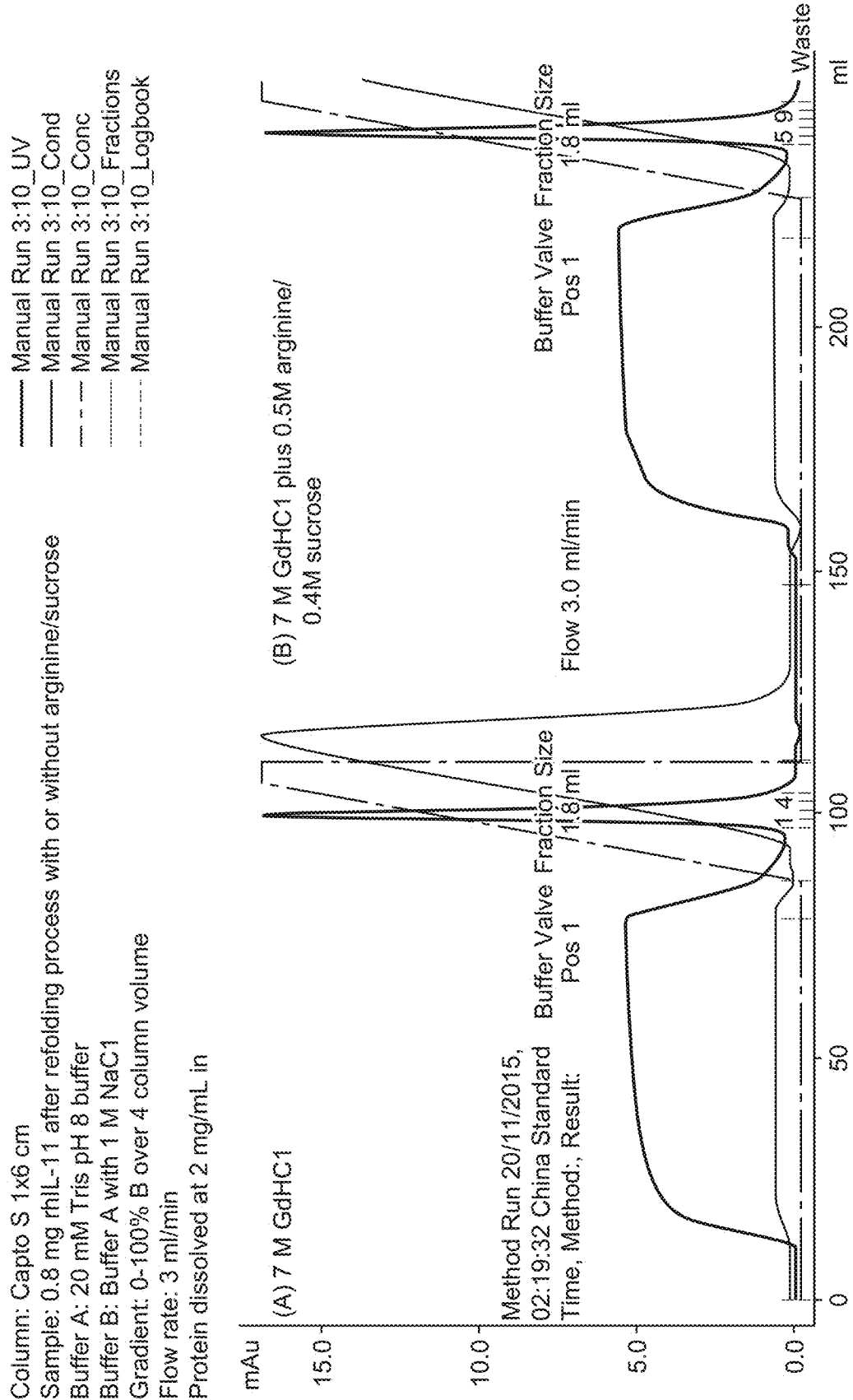
FIG. 8 shows the results of isolation of refolded rhIL-11 in the presence or in the absence of co-solutes. The red trace depicts in-line conductivity and the blue trace depicts UV absorbance at 280 nm.

Many co-solutes, which act as folding enhancers or aggregation suppressors, can be introduced to assist in protein refolding. Typical co-solutes include PEG, cyclodextrin, arginine, proline, and sucrose. The mechanism of action for these co-solutes is not clear. Inventors studied the effects of two co-solutes, 0.5 M arginine and 0.4 M sucrose, which were added to the refolding solution. After refolding by dilution, refolded rhIL-11 of each preparation was isolated with a cation exchanger as described above. The yield of refolding was evaluated by evaluating peak height (typical results are shown in FIG. 8), and show similar yields of refolded rhIL-11. The Inventors have found that neither arginine nor sucrose facilitate the refolding of rhIL-11, and that the use of co-solutes can be eliminated from the rhIL-11 purification process. This advantageously simplifies downstream purification processes.

Figure 9:
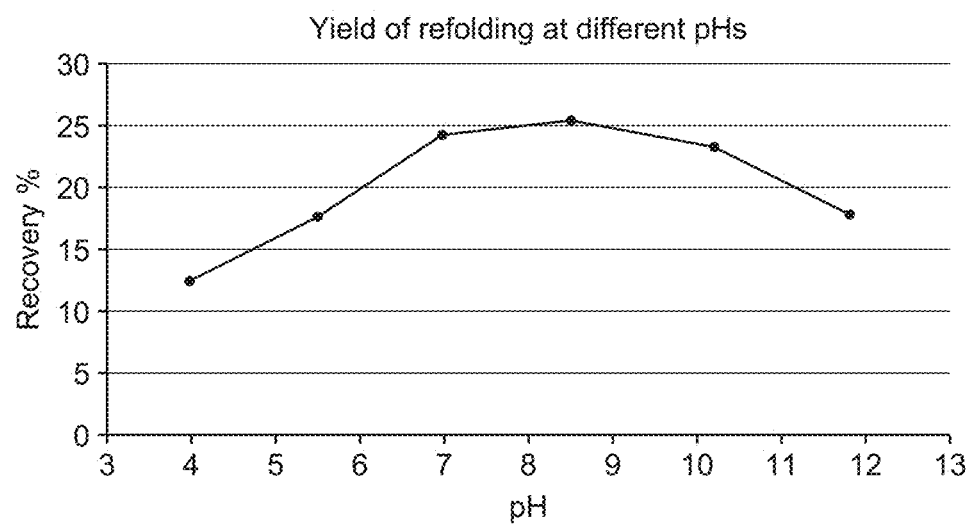
FIG. 9 shows the refolding yield of rhIL-11 at different pHs.

The pH for refolding was optimized by dissolving the protein precipitate generated by PEG treatment at various pHs. Protein from 2 mL fermentation medium was collected after PEG precipitation was reconstituted at 2 mg/mL in 7 M GdHCl buffer at different pH values. After refolding by simple dilution using a corresponding pH solution, refolded rhIL-11 of each preparation was isolated with a cation exchanger using the procedure described above. The yield of refolding was evaluated by comparing observed peak area to that produced by a reference standard of rhIL-11, as shown in FIG. 9. Refolding was found at all pH values studied, and showed a broad optimum at about pH 8.5.

Isolation of Refolded rhIL-11 Using Cation-Exchange Chromatography

Figure 10:
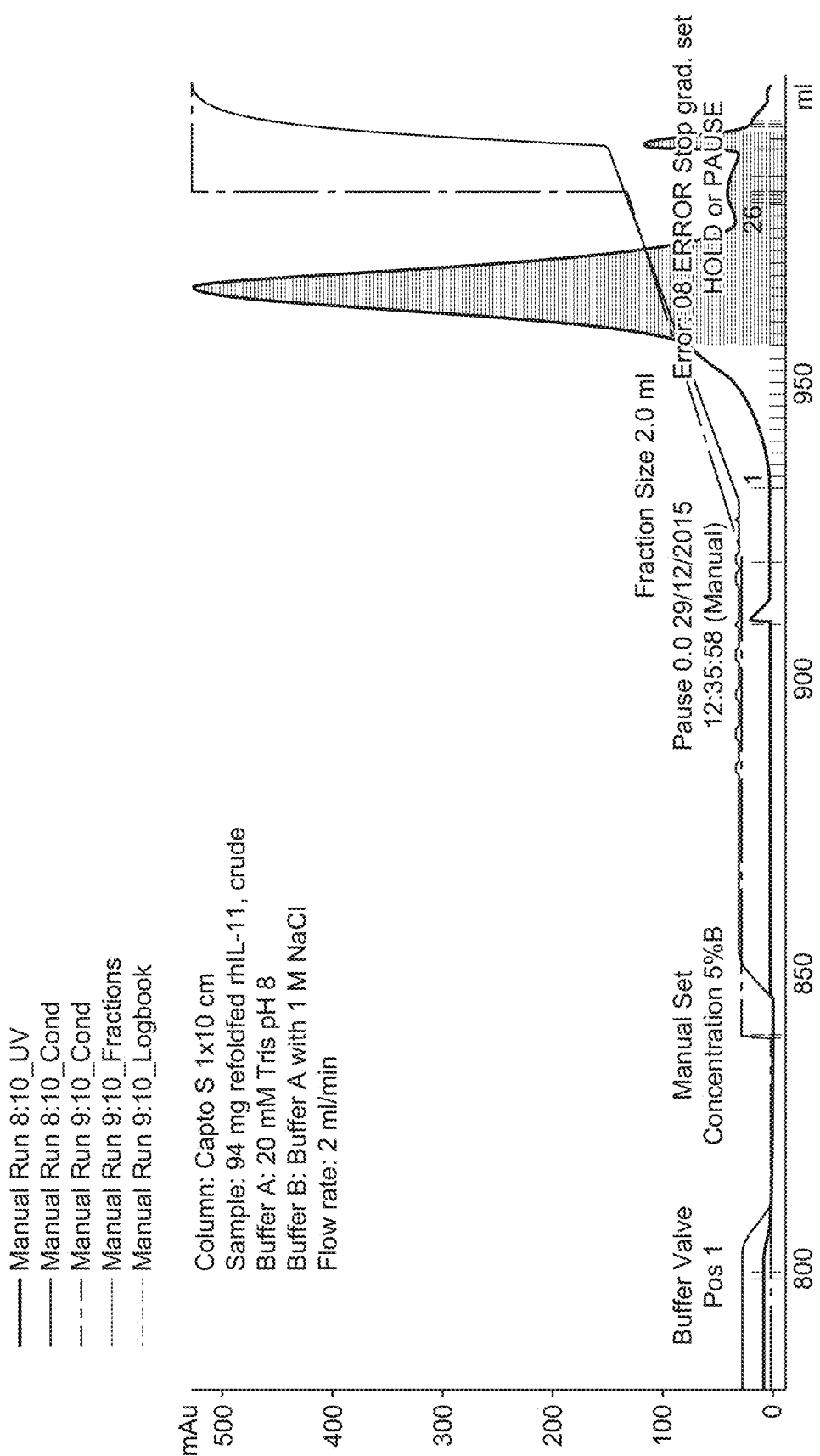
FIG. 10 shows the results of isolation of renatured rhIL-11 by liquid chromatography using a CAPTO-S column (a cation exchanger). The red trace depicts in-line conductivity, the green trace depicts pH, and the blue trace depicts UV absorbance at 280 nm. The shaded region represents fractions judged suitable for pooling.
Figure 11A:
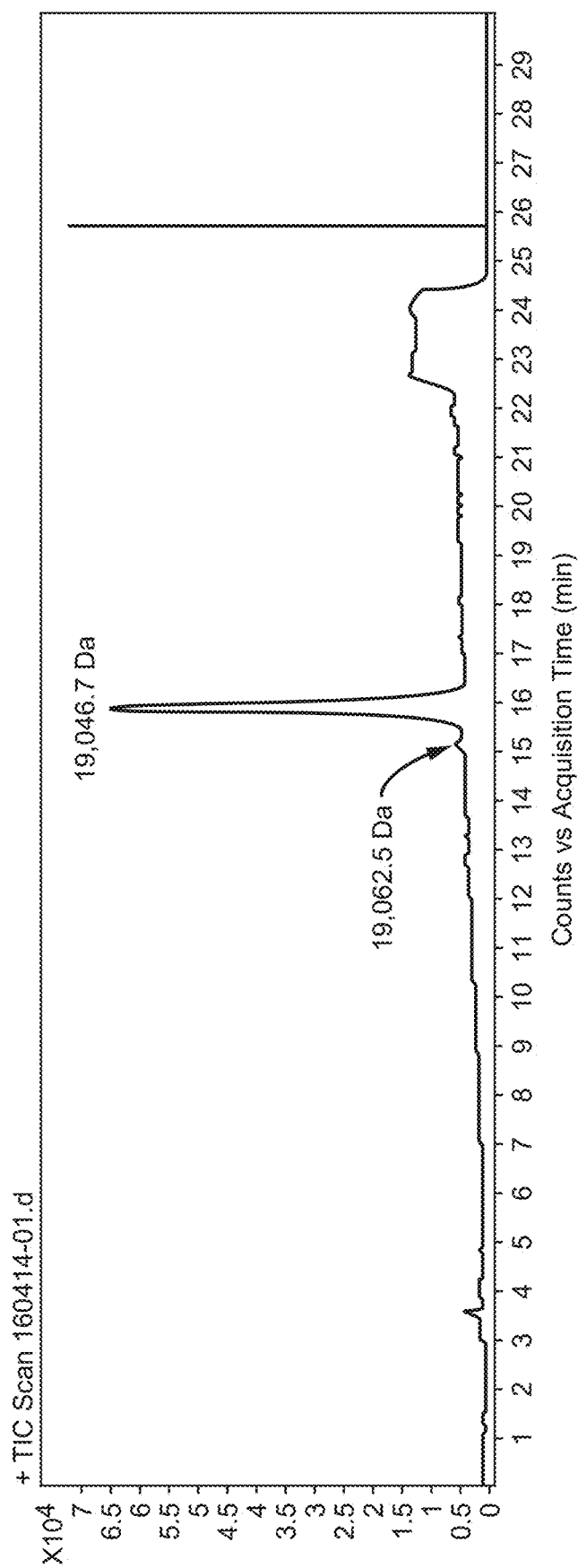
FIGS. 11A and 11B show the results of molecular mass determination by LC/MS.
Figure 11B:
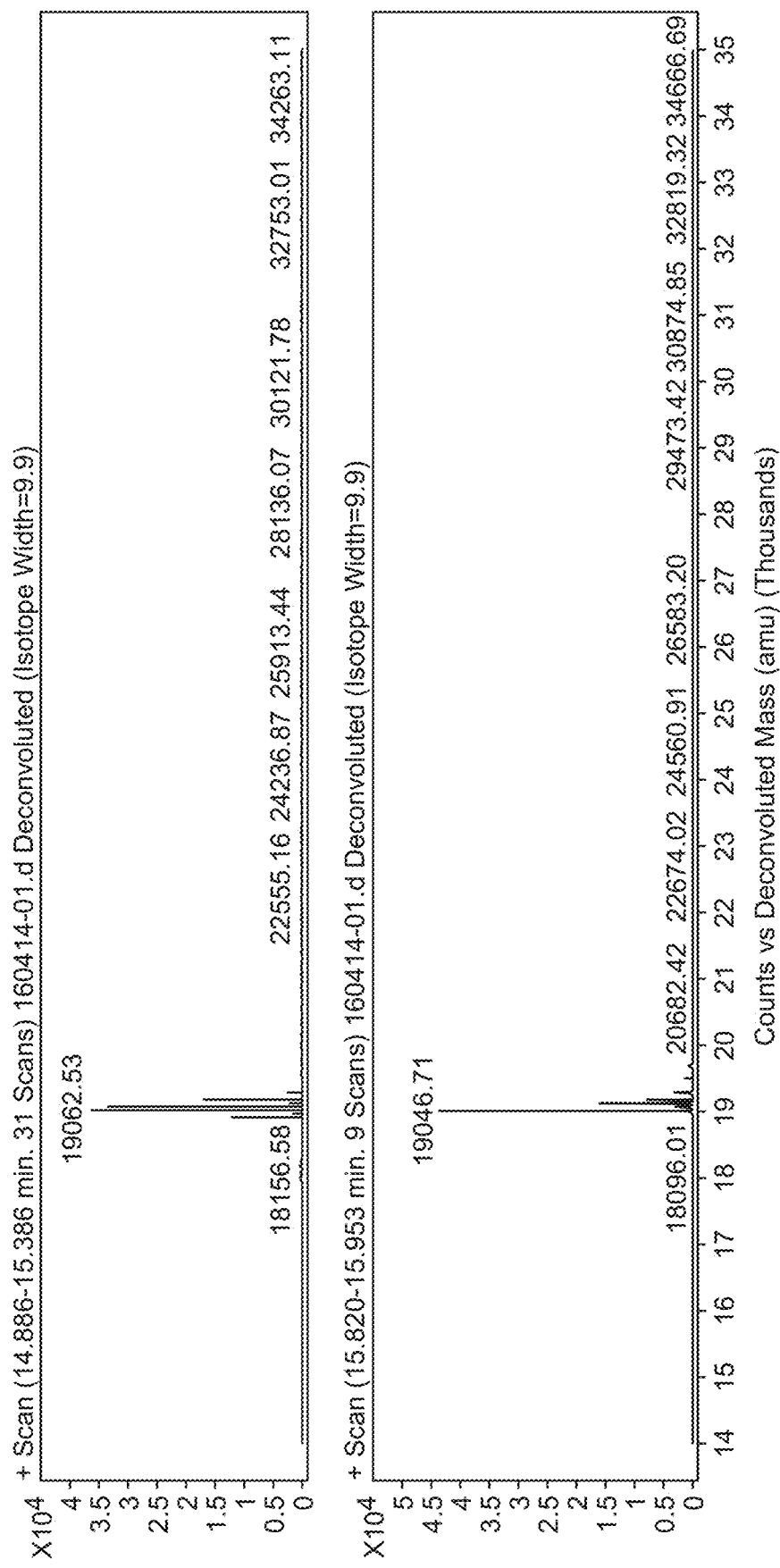

Isolation using cation exchange media was investigated using 236 mL of fermentation medium containing about 94.2 mg secretory rhIL-11. Protein was precipitated with 8% PEG 8000 (w/v) and recovered by centrifugation at 4,000 rpm for 15 minutes. After discarding the supernatant the solid phase was reconstituted to 2 mg/mL protein concentration with 20 mM sodium phosphate pH 8 buffer containing 7 M GdHCl. The protein solution was incubated at room temperature for an hour with gentle stirring to allow complete solubilization. The renaturing/refolding process was initiated by pouring the protein solution into a 10-fold volume of guanidine-free 4 mM sodium phosphate pH 8 buffer. The resulting solution was further incubated at room temperature for another hour, followed by buffer exchange using ultrafiltration or direct dilution with additional buffer solution to achieve a conductivity of less than 6 mS/cm. Cation-exchange chromatography was conducted using a CAPTO-S column (1 cm×10 cm), with typical results shown in FIG. 10. After loading onto the column at a sample load of 12 mg/mL resin, the column was washed using 50 mM NaCl buffer, followed by application of a 50-300 mM NaCl gradient over 10 column volumes. Fractions containing rhIL-11 (as indicated by non-reducing SDS-PAGE) were combined in a pool, providing a step yield of about 40% to about 60%. The product was also analyzed by RP-UPLC coupled with mass spectrometry to elucidate the molecular mass of purified protein (see FIG. 11). The deconvoluted mass of the predominant peak observed on UPLC was 19046.7 Da, agreeing with the theoretical averaged mass of rhIL-11 at 19,047 Da. The small peak ahead of rhIL-11 in the liquid chromatogram (accounting for 8.6%) is thought to represent the oxidized species, as its deconvoluted mass was 15.8 Da greater than that of rhIL-11 corresponding to about the mass of a single oxygen (16 Da). The purified rhIL-11 after refolding process was consequently subject to a cell-based assay, suggesting full recovery of activity via renaturing process (data not shown).

Figure 12:
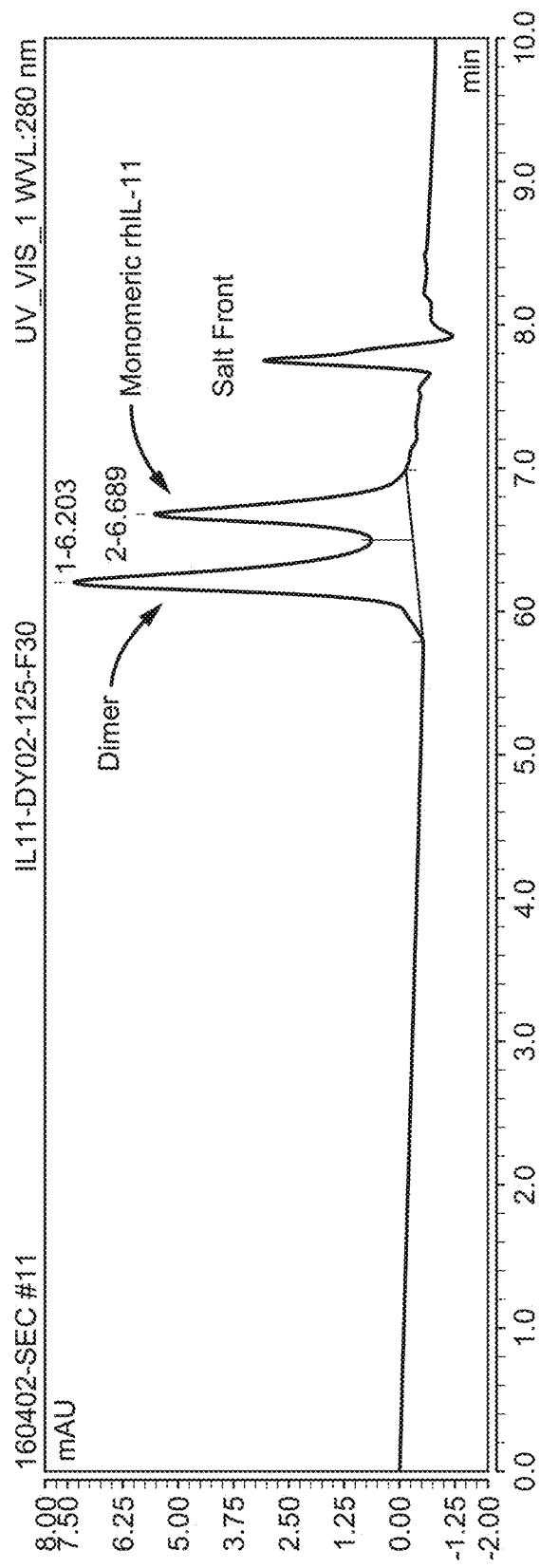
FIG. 12 shows results of size-exclusion chromatography of an elution fraction of the predominant peak from ion exchange over a CAPTO-S column.

The small shoulder eluting after the predominant peak from the CAPTO-S column was further investigated. RP-UPLC analysis coupled with MS indicated a single peak with the same retention time as the rhIL-11 reference standard, and with a molecular weight agreeing with its theoretical mass (data not shown). SDS-PAGE analysis also revealed identical migration position with an rhIL-11 reference standard (data not shown). In size-exclusion chromatography using 25 mM sodium phosphate pH 7.0 containing 0.5 M NaCl as an eluent, this small shoulder eluted as a doublet rather than a single peak. One peak of the doublet eluted with a retention time identical to that of native rhIL-11, where the remaining peak eluted earlier and is thought to be a dimeric form (see FIG. 12). Since subsequent purification using hydrophobic interaction chromatography with 0.5 M ammonium sulfate can potentially disrupt such aggregates these fractions were combined with the main pool.

Reduction of Oxidized rhIL-11 by Adding Peptone of Non-Animal Origin to Fermentation Media Protein oxidation is a very common source of product-related impurity during manufacturing processes, resulted from constantly exposure to various forms of reactive oxygen species (ROS), such as oxygen radicals, during aerobic fermentation (which was undertaken using a basal medium plus 0.9% ammonium sulfate as nitrogen source). After purification from a CAPTO-S column, the resulting oxidized rhIL-11 content of the purified rhIL-11 was about 12.6% as quantified by RP-UPLC. In order to reduce the content of oxidative products ammonium sulfate was replaced with 0.5% phytone peptone. Phytone peptone is derived from soy peptone, which includes sulfur-containing amino acids that can not only provide a nitrogen source but also eliminate or reduce formation of ROS during fermentation. Inventors believe that supplementation of fermentation media with other sulfur-containing peptides, amino acids (e.g. cysteine, methionine), and/or organic compounds can provide similar effects. After purification by CAPTO-S column the amount of resulting oxidative rhIL-11 in the modified fermentation medium was reduced to about 6.6%, close to a proposed acceptance criteria of 5.0%. The product was further polished by in a second chromatography step to remove oxidized rhIL-11 using hydrophobic-interaction chromatography.

Removal of Oxidized rhIL-11 with Hydrophobic-Interaction Chromatography

Figure 13:
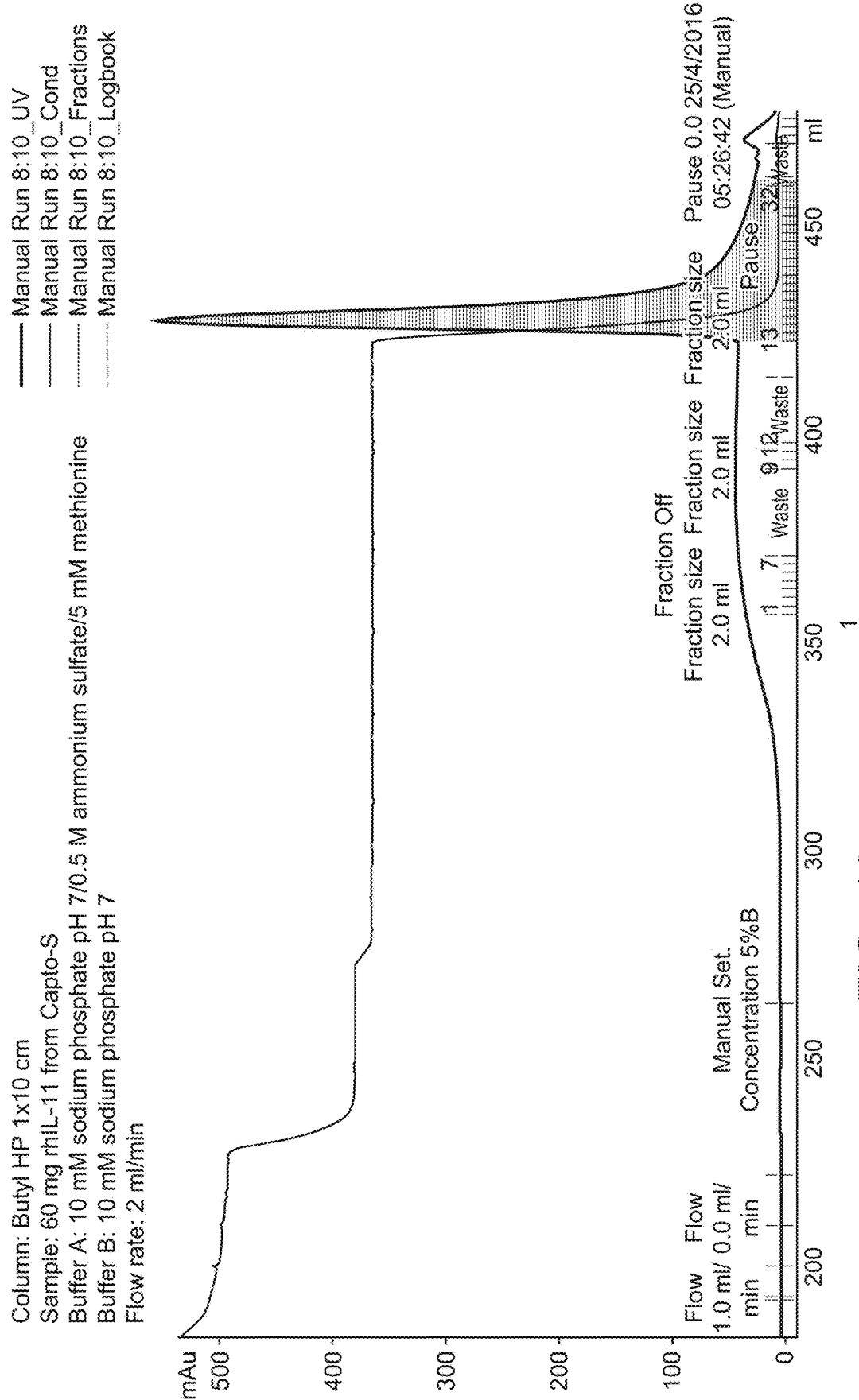
FIG. 13 shows typical results of polishing rhIL-11 by hydrophobic-interaction chromatography, using a butyl HP column to remove oxidized rhIL-11. The red trace depicts the in-line conductivity and the blue trace depicts UV absorbance at 280 nm. The shaded region represents fractions judged suitable for pooling.

To a combined pool of fractions eluted from a CAPTO-S column, solid DL-methionine was introduced to achieve a concentration of about 5 mM and solid ammonium sulfate was added to obtain a concentration of about 0.5 M. After filtration through a 0.2 or 0.45 μm membrane, the resulting protein solution was loaded on to a Butyl HP column (1 cm×10 cm) at a sample loading of 8 mg/mL bed volume, followed by washing with a buffer solution containing 0.5 M ammonium sulfate. The column was subsequently washed with over 15 column volumes of a buffer solution containing 0.475 M ammonium sulfate. Polished rhIL-11 product was eluted using 10 mM sodium phosphate pH 7 buffer (see FIG. 13). The oxidized rhIL-11 content of each fraction was quantified by RP-UPLC, and showed a decreased content of oxidized species. Fractions containing less than 5% oxidized species were pooled, and provided a step recovery of about 49%.

Buffer Change and Concentration

The resulting product eluted from the Butyl HIC column contained a large amount of ammonium sulfate that was subsequently removed by extensive dialysis and/or ultrafiltration against 10 mM sodium phosphate pH 7 buffer. The concentration was adjusted to greater than 6 mg/mL for cold storage.

Characterization of the rhIL-11 Product

Figure 14:
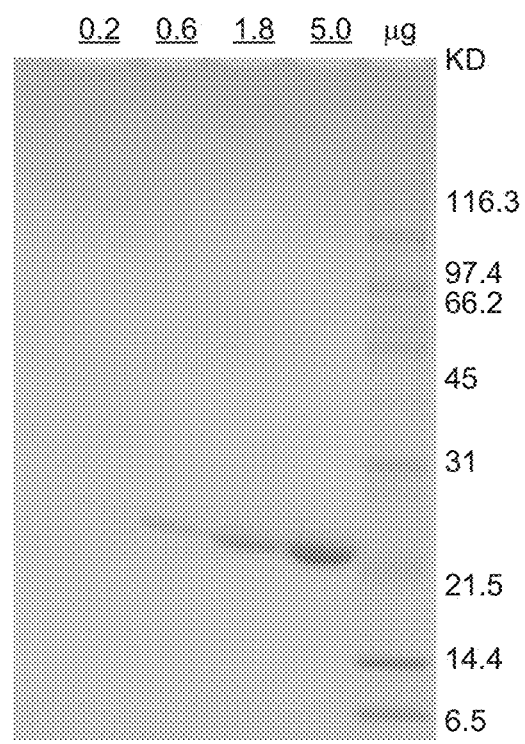
FIG. 14 shows typical results of purity studies of the purified rhIL-11, using non-reducing 16% SDS-PAGE stained with Coomassie brilliant blue. Protein samples were loaded from 0.2 to 5.0 µg.

The final purified bulk rhIL-11 was subjected to various analyses including identity, purity and potency. The purity and relative molecular weight were analyzed by non-reducing SDS-PAGE using a 16% gel (as shown in FIG. 14), which showed a single band at high purity.

Figure 15:
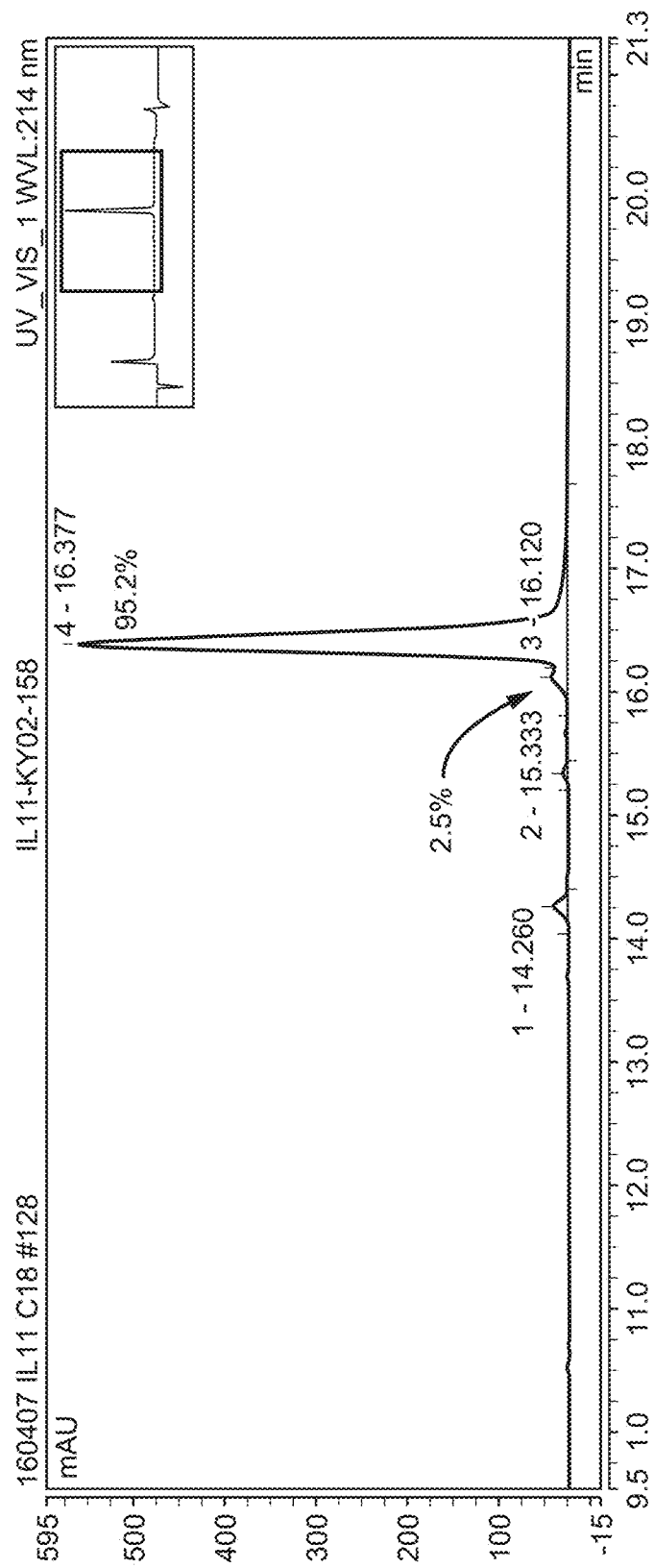
FIG. 15 shows typical results of purity studies of rhIL-11 and related proteins assayed by RP-UPLC. The oxidized rhIL-11 was present at about 2.5% while unknown impurities were present at about 1.6%.
Figure 16:
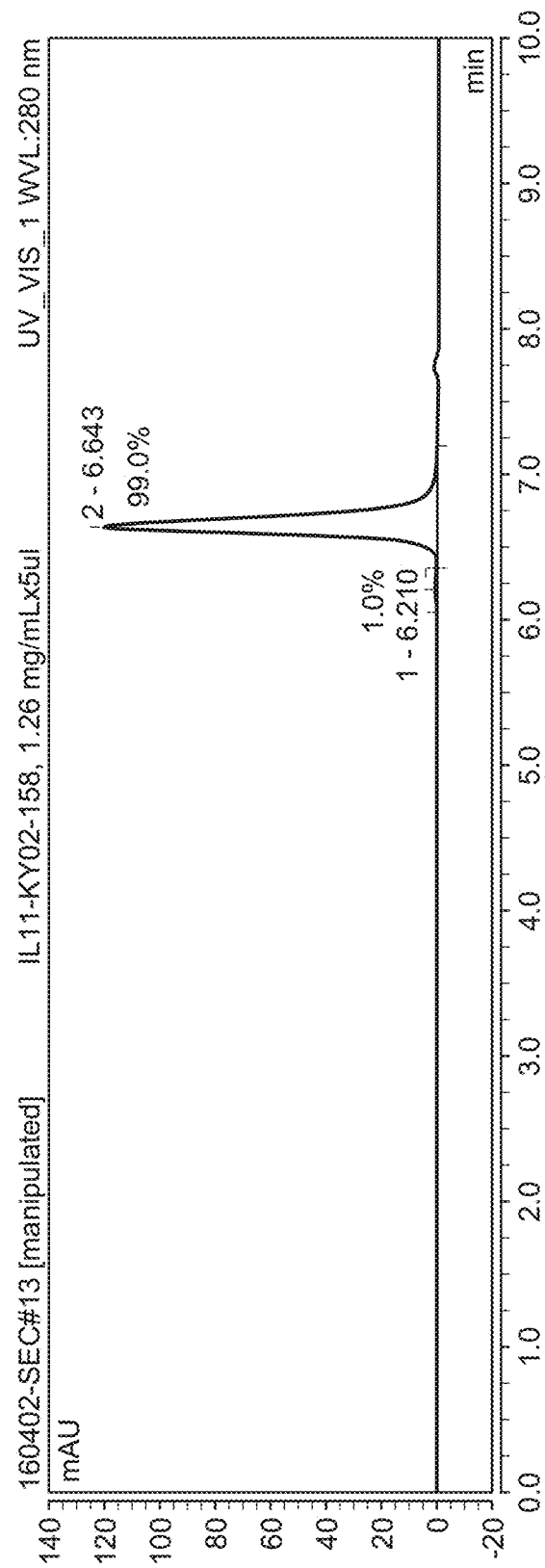
FIG. 16 shows typical results of purity studies of monomeric rhIL-11 as determined by SEC-UPLC. The purity of monomeric rhIL-11 was about 99.0%.

Purity (and related impurities) was determined by RP-UPLC. As shown in FIG. 15, the purity of rhIL-11 was greater than 95%. The rhIL-11 preparation contained about 2.5% oxidized rhIL-11, which is comparable to the 2.4% content of a commercial product (Nemega). Monomeric rhIL-11 content was quantified by SEC-UPLC as shown in FIG. 16, indicating a purity at 99%.

Figure 17:
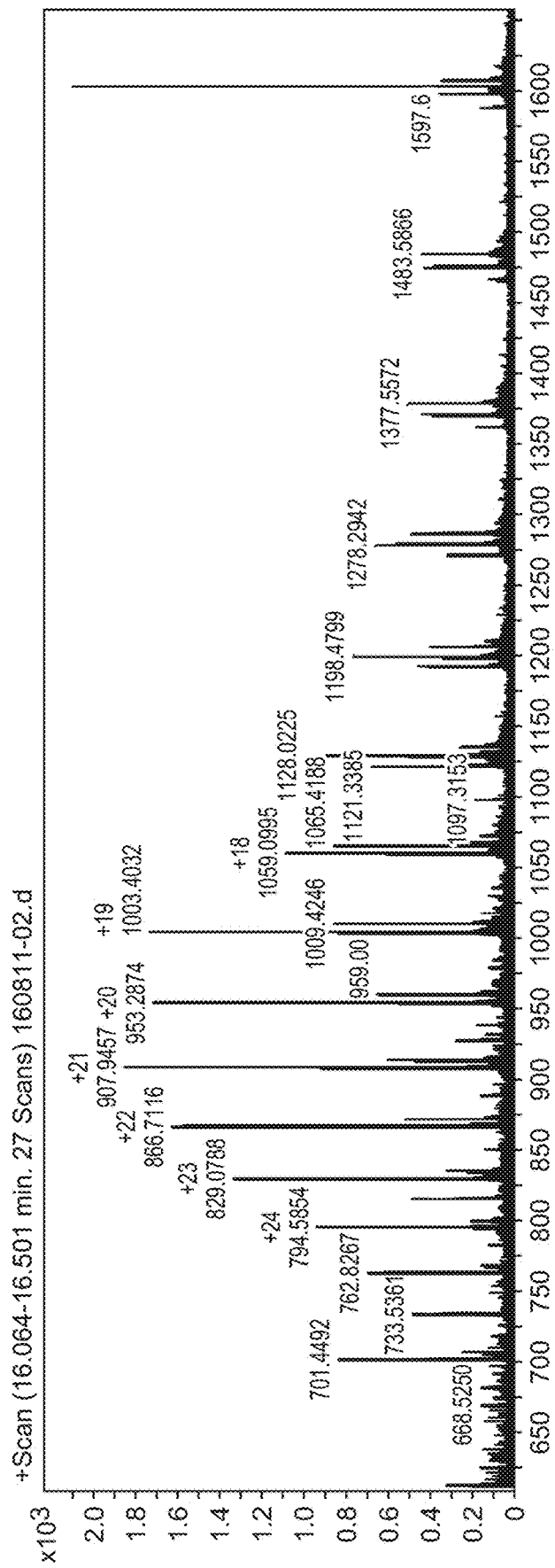
FIG. 17 provides a mass spectrum m/z of the purified IL-11 product. A deconvoluted mass 19,045.7 Da was obtained, agreeing with the expected molecular weight 19,047 Da.
Figure 18:
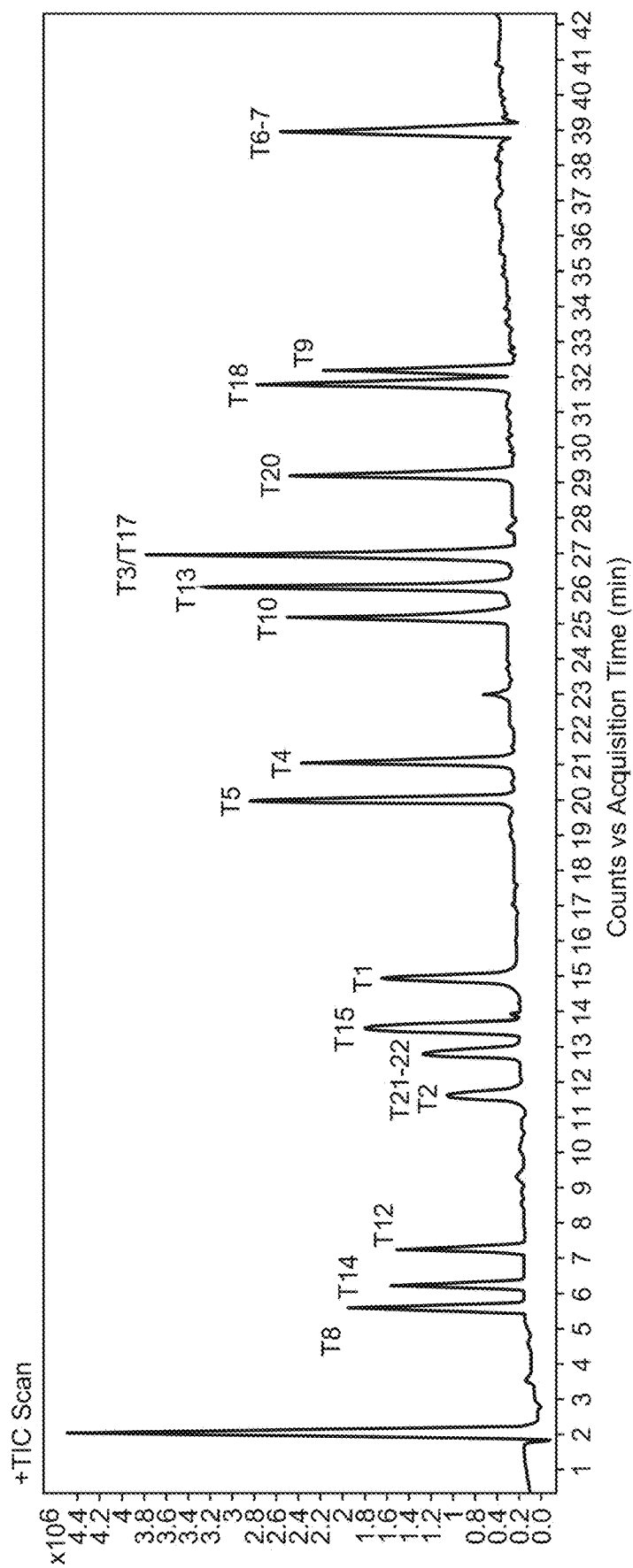
FIG. 18 shows a typical total ion chromatogram of tryptic peptides derived from hydrolysis of rhIL-11. The identification of each peptide was confirmed by m/z and MS/MS fragmentation.

The molecular mass of the purified rhIL-11 was determined by LC-MS, exhibiting a deconvoluted mass at 19,045.7 Da (see FIG. 17). This is in good agreement with the theoretical averaged molecular weight of 19,047 Da (deviation −68.2 ppm). In addition the amino acid sequence of purified rhIL-11 was characterized by peptide mapping coupled with LC-MS. Protein was digested by trypsin, which selectively hydrolyzes peptide bonds on the C-terminal side of lysine and arginine amino acid residues. The identity of each peak was determined by m/z ratio and MS/MS fragmentation. All proteolytic peptides were successfully assigned (as shown in FIG. 18) except T11, T16 and T19, providing a sequence coverage of 88.7%.

The N-terminal amino acid sequence was determined using an Applied Biosystems LC 494 PROCISE® Protein Sequencing System, confirming the initial 15 amino acids as: Gly-Pro-Pro-Pro-Gly-Pro-Pro-Arg-Val-Ser-Pro-Asp-Pro-Arg-Ala (SEQ ID NO. 15). Hydrolyzed amino acid composition was determined following a sample pretreatment with 6N HCl hydrolysis under nitrogen at 110° C. for 22 hrs. Under such an acidic hydrolysis condition, asparagine and glutamine are deamidated to form respective acids. Tryptophan is completely degraded. Cysteine and methionine are oxidized and are not readily detected from the acid hydrolysate. Tyrosine, serine and threonine are partially hydrolyzed. Results of amino acid composition studies are shown in Table 5. The mole ratios of most amino acids are in good agreement with expected values. Inventors believe that the results observed for isoleucine, tyrosine and phenylalanine were impacted by their relatively low abundance.

TABLE 5

|  | 1-fold dilution | | | 5-fold dilution | | | | Expected | | |
|---|---|---|---|---|---|---|---|---|---|---|
|  | nmole/20 uL in resuspended solution | | | | | | | Calc. No. | No. of | ABS. % |
|  | Prep. 1 | Prep. 2 | Prep. 3 | Prep. 1 | Prep. 2 | Prep. 3 | Mean | of residue | residue | Deviation |
| Asp + Asn | 2.374 | 2.327 | 2.372 | 2.460 | 2.270 | 2.360 | 2.361 | 11.36 | 12 | 5.35 |
| Thr | 1.807 | 1.711 | 1.741 | BD | BD | BD | 1.753 | 8.43 | 9 | 6.28 |
| Ser | 2.250 | 2.118 | 2.166 | 2.305 | 2.120 | 2.205 | 2.194 | 10.56 | 11 | 4.03 |
| Glu + Gln | 2.190 | 2.123 | 2.160 | 2.385 | 2.200 | 2.295 | 2.226 | 10.71 | 10 | 7.08 |
| Gly | 2.977 | 2.793 | 2.853 | 2.945 | 2.705 | 2.835 | 2.851 | 13.72 | 14 | 2.01 |
| Ala | 4.177 | 3.917 | 3.998 | 4.190 | 3.850 | 4.030 | 4.027 | 19.38 | 20 | 3.12 |
| Cys | N/A | N/A | N/A | N/A | N/A | N/A | N/A | N/A | 0 | N/A |
| Val | 0.818 | 0.705 | 0.707 | BD | BD | BD | 0.743 | 3.58 | 5 | 28.47 |
| Met | N/A | N/A | N/A | N/A | N/A | N/A | N/A | N/A | 2 | N/A |
| Ile | 0.249 | 0.239 | 0.239 | 0.255 | 0.230 | 0.235 | 0.241 | 1.16 | 2 | 41.98 |
| Leu | 8.888 | 8.406 | 8.549 | 8.750 | 8.120 | 8.415 | 8.521 | 41.00 | 41 | 0.00 |
| Tyr | 0.250 | 0.234 | 0.239 | 0.660 | 0.595 | 0.565 | 0.424 | 2.04 | 1 | 103.93 |
| Phe | 0.312 | 0.380 | 0.385 | 0.585 | 0.575 | 0.565 | 0.467 | 2.25 | 1 | 124.69 |
| Lys | 0.608 | 0.660 | 0.673 | BD | BD | BD | 0.647 | 3.11 | 3 | 3.77 |
| His | 0.742 | 0.743 | 0.755 | BD | BD | BD | 0.747 | 3.59 | 4 | 10.19 |
| Arg | 3.471 | 3.276 | 3.317 | 3.370 | 3.090 | 3.195 | 3.287 | 15.81 | 18 | 12.15 |
| Pro | 3.854 | 3.651 | 3.729 | 5.270 | 5.195 | 5.170 | 4.478 | 21.55 | 21 | 2.60 |
| Trp | N/A | N/A | N/A | N/A | N/A | N/A | N/A | N/A | 3 | N/A |

N/A: Not applicable.
BD: Below detection limit.
Optimal concentration range is 0.4-10 nmole/20 μL.

Figure 19:
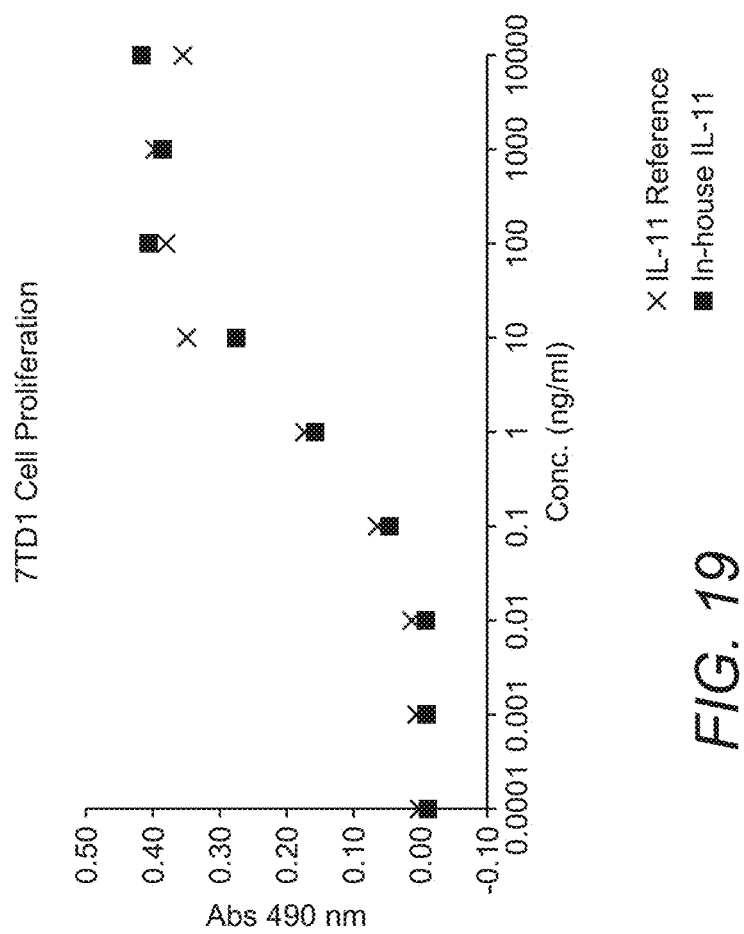
FIG. 19 shows typical results of a cell proliferation assay performed using the purified rhIL-11.

The bioactivity of the purified rhIL-11 was determined us a 7TD1 cell proliferation assay; typical results are shown in FIG. 19. The observed EC50s were 1.1 and 2.2 ng/mL for the reference rhIL-11 and the rhIL-11 produced by the described method respectively, suggesting comparable potency.

As shown above, the inventive concept provides a novel method for production and of isolation of highly purified rhIL-11 using yeast. Secretory recombinant human interleukin-11 was successfully expressed by *Pichia pastoris*, however the expression product was inactive biologically due to self-aggregation of rhIL-11. Addition of a non-ionic surfactant such as TWEEN-80 in a high-density fed-batch culture only yielded bioactive product at about 10% of total rhIL-11. The addition of TWEEN-80, however, can result in foaming due to agitation during the fermentation process.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

1. Du X X, Williams D A. Interleukin-11: A Multifunctional Growth Factor Derived from the Hematopoietic Microenvironment. Blood. 1994; 83(8):2023-30.
2. Unattributed Editorial; Transgenic Milk Prospects Turn Sour. Nat Biotech. 2006; 24(4):368.
3. McCoy J, DiBlasio-Smith E, Grant K, Vallie E L, inventors; Genetics Institute, assignee. Peptide and Protein Fusions to Thioredoxin, Thioredoxin-like Molecules and Modified Thioredoxin-like Molecules. U.S. Pat. No. 5,646,016. 1997.
4. Jung Y, Ho S-H, Park M-O, Kim M-S, inventors Biopolymer Conjugates Comprising an Interleukin-11 Analog. USA patent application 2010/0098658. 2010.
5. Cox-III G, inventor; Bolder Biotechnology, Inc., assignee. Cysteine Variants of Interleukin-11. U.S. Pat. No. 8,133,480. 2012.
6. Wang T Y, Wang C M, Wei G, Qiu J W, Huang Y S. Expression of the Recombinant Human Interleukin-11 in *Pichia pastoris*. Acta Biochimica et Biophysica Sinica. 2001; 33(6):659-64.
7. Qiu J, Wang T, Liu G-A, inventors; Jiuyuan Gene Engineering Co. Ltd., assignee. Method for Producing Recombinant Human Interleukin-11 using Methyl Alcohol Yeast. China patent 1288062A. 2001.
8. Huang Y, Ma K, Yang T, Sun H, Shu F, Chou J, inventors; Jiuyuan Gene Engineering Co. Ltd., assignee. Production method for *Pichia pastoris* expression recombinant human interleukin 11. Chinese patent 102329388. 2013.
9. Hong E, Davidson A R, Kaiser C A. A Pathway for Targeting Soluble Misfolded Proteins to the Yeast Vacuole. The Journal of cell biology. 1996; 135(3):623-33.
10. Gasteiger E, Hoogland C, Gattiker A, Duvaud S, Wilkins M, Appel R, et al. Protein Identification and Analysis Tools on the ExPASy Server. In: Walker JM, editor. The Proteomics Protocols Handbook. USA: Humana Press Inc.; 2005. p. 571-607.
11. Hart R A, Lester P M, Reifsnyder D H, Ogez J R, Builder S E. Large Scale, in situ Isolation of Periplasmic IGF-I from *E. coli*. Bio/Technology (Nature Publishing Company). 1994; 12(11):1113-7.
12. Karow J, Hudson K R, Hall M A, Vernallis A B, Taylor J A, Gossler A, et al. Mediation of Interleukin-11-Dependent Biological Responses by a Soluble Form of the Interleukin-11 Receptor. The Biochemical journal. 1996; 318 (Pt 2):489-95.
13. Ozols J. Amino acid analysis. Methods in Enzymology. 1990; 182:587-601.
14. Bahrami A, Shojaosadati S A, Khalilzadeh R, Mohammadian J, Farahani E V, Masoumian M R. Prevention of Human Granulocyte Colony-Stimulating Factor Protein Aggregation in Recombinant *Pichia pastoris* Fed-Batch Fermentation using Additives. Biotechnology and applied biochemistry. 2009; 52(Pt 2):141-8.
15. Tsumoto K, Ejima D, Kumagai I, Arakawa T. Practical Considerations in Refolding Proteins from Inclusion Bodies. Protein Expression and Purification. 2003; 28(1):1-8.
16. Yokota H, Saito H, Masuoka K, Kaniwa H, Shibanuma T. Reversed Phase HPLC of Met58 Oxidized rhIL-11: Oxidation Enhanced by Plastic Tubes. Journal of Pharmaceutical and Biomedical Analysis. 2000; 24(2):317-24.
17. Fan S B, Kogoma T. Oxidative Stress Responses in *Escherichia coli* and *Salmonella typhimurium*. Microbiological Reviews. 1991; 55(4):561-85.
18. Shacter E. Quantification and Significance of Protein Oxidation in Biological Samples. Drug Metabolism Reviews. 2000; 32(3-4):307-26

What is claimed is:

1. A method for producing interleukin 11 (IL-11), comprising:
   introducing an expression vector encoding for a recombinant IL-11 into a yeast, wherein the recombinant IL-11 is not in the form of a fusion protein;
   culturing the yeast in a culture media under conditions to induce expression of IL-11;
   following culturing of the yeast, removing solids from the culture media to produce a supernatant;
   contacting the supernatant with a polyethylene glycol having an average molecular weight of about 2,000 D to about 20,000 D in quantities sufficient to form a suspension comprising a precipitate, wherein the polyethylene glycol is present in the supernatant at from about 4% (w/v) to about 12% (w/v) after contacting;
   collecting the precipitate;
   solubilizing the precipitate in a solution comprising guanidine hydrochloride at a concentration of about 4M to 10M to produce a crude IL-11 solution;
   reducing the guanidine hydrochloride concentration to 0.7M or less at a pH of about 4 to about 12 and at an IL-11 concentration of 0.1 mg/ml to 10 mg/mL to produce a refolded IL-11 solution;
   contacting the refolded IL-11 solution with a cation exchange media; and
   eluting a purified IL-11 from the cation exchange media.

2. The method of claim 1, wherein the step of reducing the guanidine hydrochloride comprises incubating for about one hour at 18° C. to 25° C. following reduction of the guanidine hydrochloride concentration.

3. The method of claim 1, comprising the further steps of:
   contacting the purified IL-11 with a hydrophobic interaction media; and
   eluting a polished IL-11 from the hydrophobic interaction media,
   wherein the polished IL-11 has a reduced content of oxidized IL-11 relative to the purified IL-11.

4. The method of claim 3, wherein the hydrophobic interaction media is selected from the group consisting of butyl, hexyl, octyl, and phenyl.

5. The method of claim 4, wherein the polished IL-11 has a purity of at least 95%.

6. The method of claim 3, wherein the polished IL-11 comprises about 5% or less oxidized IL-11.

7. The method of claim 3, wherein the polished IL-11 comprises about 1% or less dimers of IL-11.

8. The method of claim 1, wherein the step of producing the refolded IL-11 solution is performed in the absence of co-solutes.

9. The method of claim 1, wherein the step of producing the refolded IL-11 solution is performed at a pH of about 7 to about 11.

10. The method of claim 1, wherein the purified IL-11 has a biological activity of about $4 \times 10^6$ U/mg to about $1.2 \times 10^7$ U/mg when tested using the 7TD1 cell line, wherein the biological activity is cell proliferation.

11. The method of claim 10, wherein the purified IL-11 has a biological activity of about $6 \times 10^6$ U/mg when tested using the 7TD1 cell line, wherein the biological activity is cell proliferation.

* * * * *